US009629853B2

(12) United States Patent
Jones et al.

(10) Patent No.: US 9,629,853 B2
(45) Date of Patent: Apr. 25, 2017

(54) USES OF GANAXOLONE

(71) Applicant: WISCONSIN ALUMNI RESEARCH FOUNDATION, Madison, WI (US)

(72) Inventors: Mathew Victor Jones, Madison, WI (US); Chiara Cirelli, Verona, WI (US); Kile Patrick Mangan, Madison, WI (US); Aaron B. Nelson, New York, NY (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/718,524

(22) Filed: May 21, 2015

(65) Prior Publication Data
US 2015/0335659 A1 Nov. 26, 2015

Related U.S. Application Data

(60) Provisional application No. 62/001,347, filed on May 21, 2014.

(51) Int. Cl.
*A61K 31/57* (2006.01)
*A61K 49/00* (2006.01)
*C12Q 1/68* (2006.01)

(52) U.S. Cl.
CPC .......... *A61K 31/57* (2013.01); *A61K 49/0008* (2013.01); *C12Q 1/68* (2013.01); *C12Q 1/6883* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 5,120,723 | A | 6/1992 | Gee et al. |
|---|---|---|---|
| 5,208,227 | A | 5/1993 | Gee et al. |
| 5,232,917 | A | 8/1993 | Bolger et al. |
| 5,319,115 | A | 6/1994 | Tahir et al. |
| 5,591,733 | A | 1/1997 | Bolger et al. |
| RE35,517 | E | 5/1997 | Gee et al. |
| 8,318,714 | B2 | 11/2012 | Shaw et al. |
| 8,362,286 | B2 | 1/2013 | Shaw et al. |
| 8,618,087 | B2 | 12/2013 | Shaw et al. |

OTHER PUBLICATIONS

Pieribone et al (Epilepsia 48:1870-1874).*
Carter et al (JPET 280:1284-1295, 1997).*
Childhood Absence Epilepsy (available online at www.epilepsy.com—accessed May 15, 2016).*
Wong (Epilepsy Currents 10:131-133, 2010).*
Snead et al (Ann Neurol 44:688-691, 1998—Abstract only).*
Bouma et al.; "The Outcome of Absence Epilepsy: A Meta-analysis"; Neurology; 47; pp. 802-808 (1996).
Budziszewska et al.; "Effects of Neurosteroids on Spike-wave Discharges in the Genetic Epileptic WAG/Rij Rat"; Epilepsy Research; 33; pp. 23-29; (1999).
Carter et al.; "Characterization of the Anticonvulsant Properties of Ganaxolone (CCD 1042; 3-Alpha-Hydroxy-3-Beta-methyl-5-Alpha-pregnan-20-one), a Selective, High-Affinity, Steroid Modulator of the y-Aminobutyric Acid(A) Receptor"; J of Pharmacology and Experimental Therapeutics; 280(3); pp. 1283-1295; (1997).
Citraro et al.; "Effects of Some Neurosteroids Injected into Some Brain Areas of WAG/Rij Rats, an Animal Model of Generalized Absence Epilepsy"; Neuropharmacology; 50; pp. 1059-1071; (2006).
Coenen et al.; "Effects of the GABA-uptake Inhibitor Tiagabine on Electroencephalogram, Spike-wave Discharges and Behaviour of Rats"; Epilepsy Research; 21; pp. 89-94; (1995).
Cope et al.; "Enhanced Tonic GABA(A) Inhibition in Typical Absence Epilepsy"; Nature Medicine; 15(12); pp. 1392-1398; (2009).
Crunelli et al.; "Transition to Absence Seizures and the Role of GABA(A) Receptors"; Epilepsy Research; 97; pp. 283-289; (2011).
Errington et al.; "Augmentation of Tonic GABA(A) Inhibition in Absence Epilepsy: Therapeutic Value of Inverse Agonists at Extrasynaptic GABA(A) Receptors"; Advances in Pharmacological Sciences; doi: 10.1155/2011/790590; pp. 1-12; (2011).
Glauser et al.; "Ethosuximide, Valproic Acid, and Lamotrigine in Childhood Epilepsy"; New England Journal of Medicine; 362(9); pp. 790-799; (2010).
Hogenkamp et al.; "Synthesis and in Vitro Activity of 3-Beta-Substituted-3-Alpha-hydroxypregnan-20-ones:Allosteric Modulations of the GABA(A) Receptor"; J. Med. Chem. 40; pp. 61-72; (1997).
Moore et al.; "A Clinical Study of 57 Children With Fetal Anticonvulsant Syndromes"; J. Med Genet; 37; pp. 489-497; (2000).
Nohria et al.; "Ganaxolone"; The Journal of the American Society for Experimental NeuroTherapeutics; 4; pp. 102-105; (2007).
Reddy and Rogawski; "Enhanced Anticonvulsant Activity of Neuroactive Steroids in a Rat Model of Catamenial Epilepsy"; Epilepsia; 42(3); pp. 337-344; (2001).
Reddy et al.; "Ganaxolone Suppression of Behavioral and Electrographic Seizures in the Mouse Amygdala Kindling Model"; Epilepsy Research; 89; pp. 254-260; (2010).
Reddy, Doodipala Samba; "Neurosteroids-Endogenous Regulations of Seizure Susceptibility and Role in the Treatment of Epilepsy"; in Jasper's Basic Mechanisms of the Epilepsies, 4th Ed, Noebels, JL, Ed.,Bethesda, MD; pp. 1-23; (2012).

(Continued)

*Primary Examiner* — Craig Ricci
(74) *Attorney, Agent, or Firm* — Cantor Colburn LLP

(57) ABSTRACT

Absence epilepsy, a form of epilepsy characterized by nonconvulsive seizures, has proven to be refractive to conventional epilepsy therapies. It has been found that low doses of ganaxolone can be used to reduce absence seizures in subjects with absence epilepsy, particularly pediatric subjects. In addition, ganaxolone therapy is particularly useful in subjects with absence epilepsy characterized by a reduction in tonic inhibition. Low dose ganaxolone is also used to reduce sleep disruptions and to treat sleep disorders in subjects in need of such treatment.

6 Claims, 9 Drawing Sheets

(56) References Cited

OTHER PUBLICATIONS

Snead, O. Carter III, "Ganaxolone, a Selective, High-Affinity Steroid Modulator of the Gamma-Aminobutyric Acid-A Receptor, Exacerbates Seizures in Animal Models of Absence"; Annals of Neurology; 44(4); pp. 688-691; (1998).

Steiger, Axel; "Sleep and Endocrine Regulation"; Frontiers in Bioscience 8, pp. s358-376; (2003).

Tan et al.; "Reduced Cortical Inhibition in a Mouse Model of Familial Childhood Absence Epilepsy"; PNAS; 104(44); pp. 17536-17541; (2007).

Teran-Perez et al.; "Steroid Hormones and Sleep Regulation"; Mini-Reviews in Medicinal Chemistry; 12; pp. 1040-1048; (2012).

Van Luijtelaar et al, "Hormones and Absence Epilepsy"; in Encyclopedia of Basic Epilepsy Research; Philip A. Schwartzkroin, Ed.; Elservier Academic Press Amsterdam; Boston; pp. 488-495; (2009).

Wallace et al.; "Mutant GABA(A) Receptor Gamma-2-subunit in Childhood Absence Epilepsy and Febrile Seizures"; Nature Genetics; 28; pp. 49-52 (2001).

Roth et al.; "Effect of Gaboxadol on Patient-reported Measures of Sleep and Waking Function in Patients with Primary Insomnia: Results from Two Randomized, Controlled, 3-month Studies"; Journal of Clinical Sleep Medicine;6(1);pp. 30-39; (2010).

\* cited by examiner

USES OF GANAXOLONE

CROSS-REFERENCE TO RELATED APPLICATIONS

This application claims priority to U.S. Provisional Application 62/001,347 filed on May 21, 2014, which is incorporated herein by reference in its entirety.

STATEMENT REGARDING FEDERALLY SPONSORED RESEARCH & DEVELOPMENT

This invention was made with government support under NS075366 awarded by the National Institutes of Health. The government has certain rights in the invention.

FIELD OF THE DISCLOSURE

The present disclosure is related to new medical uses of the synthetic neurosteroid analogue ganaxolone.

BACKGROUND

Ganaxolone (3α-hydroxy-3β-methyl-5α-pregnan-20-one, (3α,5α)-3-hydroxy-3-methylpregnan-20-one, or CCD 1042) is a synthetic neurosteroid analogue that acts as a modulator of $GABA_A$ receptors. Ganaxolone has been tested for safety in clinical trials, and has relatively modest side effects even at very high doses. It has shown promise for treating temporal lobe seizures as well as catamenial epilepsy. Temporal lobe epilepsy is characterized by recurrent seizures that originate in the temporal lobe of the brain. Temporal lobe seizures can involve sensory changes as well as memory disturbances. Temporal lobe seizures are characterized as partial seizures, including simple and complex, and generalized seizures such as secondarily generalized tonic-clonic seizures. Catamenial epilepsy occurs in women with preexisting epilepsy and is characterized by seizure exacerbations during the menstrual cycle, such as in the premenstrual period. Ganaxolone is also under study for the treatment of posttraumatic stress disorder and Fragile-X syndrome. Ganaxolone has been approved by the U.S. FDA for the treatment of protocadherin 19 gene (PCDH19) female epilepsy.

Because ganaxolone is well-tolerated in adults and children, it is desirable to uncover additional uses for ganaxolone.

BRIEF SUMMARY

In one aspect, a method of treating absence epilepsy in a mammalian subject in need thereof comprises administering ganaxolone to the mammalian subject in an amount of 0.2 to 2 mg/kg per dose, wherein the mammalian subject has been diagnosed with absence epilepsy.

In another aspect, a method of treating absence epilepsy in a mammalian subject in need thereof comprises determining that the mammalian subject is responsive to ganaxolone therapy, and administering ganaxolone to the mammalian subject in an amount of 0.2 to 2 mg/kg per dose, wherein the mammalian subject has been diagnosed with absence epilepsy.

In yet another aspect, a method of treating sleep disruptions in a mammalian subject in need thereof comprises administering ganaxolone to the mammalian subject in an amount of 0.2 to 2 mg/kg per dose

Figure 1:
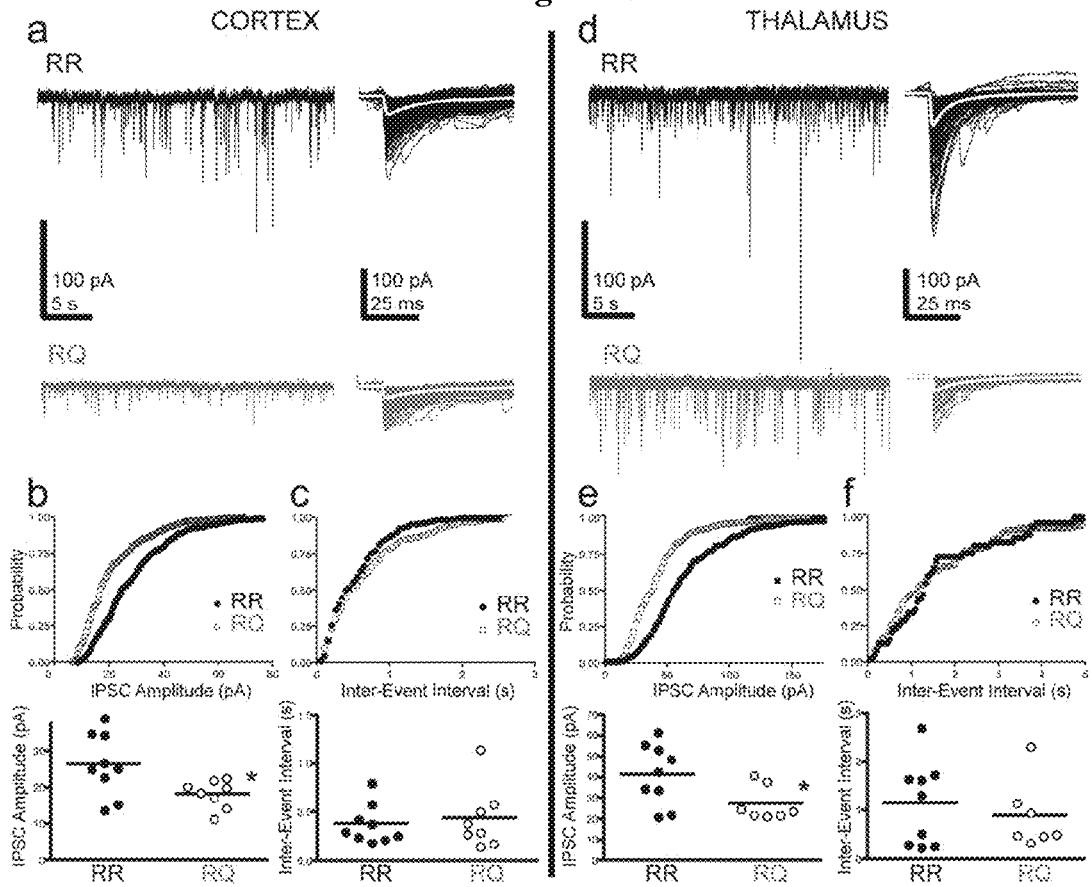
FIG. 1 shows that mIPSC (miniature inhibitory postsynaptic current) amplitude is decreased in mutant RQ mouse brain slices compared to wild type RR mouse brain slices. Panel a) Example voltage-clamp trace (left) and corresponding mIPSCs (right) for a wild type (RR) (top: black) and a mutant (RQ) (bottom: grey) cortical layer II/III pyramidal cell. Overlayed white traces are the average mIPSCs. Panel b) Cumulative amplitude distributions (top) and median mIPSC amplitudes (bottom) for cortical cells, showing a reduction in mIPSC amplitude for RQ compared to RR cortical cells ($p<0.05$, asterisk). Bars represent the mean of medians. Panel c) Cumulative interevent interval (WI) distribution (top) and medians (bottom) for cortical neurons, showing no difference in RQ compared to RR cortical neurons. Panels d-f) Same as panels a-c, but for thalamic relay neurons in RR and RQ slices.

The above-described and other features will be appreciated and understood by those skilled in the art from the following detailed description, drawings, and appended claims.

DETAILED DESCRIPTION

It has been found that ganaxolone, specifically low-dose ganaxolone, can be used to treat absence epilepsy, particularly in young subjects. Without being held to theory, it is believed that the previously studied high doses of ganaxolone used to treat other forms of epilepsy overstimulate the $GABA_A$ receptor and exacerbate the symptoms of absence epilepsy. Using low dose ganaxolone provides an optimal amount of tonic inhibition that provides normal function and reduces the symptoms of absence epilepsy in a validated mouse model. Ganaxolone provides a new treatment option for a form of epilepsy that has proven to be refractory to traditional epilepsy treatment. In addition, it has also been found that low dose ganaxolone can also be used to treat sleep disruptions and disorders, particularly to restore altered duration of NREM episodes and altered slow wave intensity back toward normal levels.

Specifically, the use of a novel animal model for absence epilepsy suggests that low dose ganaxolone reduces the occurrence of absence seizures. Whereas nearly all previous work on the relationship between GABAergic tonic inhibition and absence epilepsy has used selectively-bred polygenic rodent models (e.g., GAERS and Wag/Rij rats) that have elevated tonic inhibition, the studies presented herein use a novel knock-in mouse model (γ2R43Q knock-in mice, aka. "RQ" mice). These mice were engineered to express monogenically a mutant subunit (γ2R43Q) of the $GABA_A$ receptor that was found to cause absence epilepsy in human subjects, and like their human counterparts these mice display behavioral absence seizures and spike-wave-discharges. However, importantly, GABAergic tonic inhibition is abolished in these mice. The fact that these mice have absence epilepsy despite a lack of tonic inhibition means that the previous claim that enhanced tonic inhibition is required to induce absence epilepsy seizures is simply incorrect. It is proposed a) that there is an optimal level of tonic inhibition in the normal brain, and b) that either increases or decreases away from this optimum can cause absence epilepsy. This proposal leads to the hypothesis that rescue of tonic inhibition with ganaxolone alleviates absence seizures.

Absence epilepsy (formerly known as "petit mal epilepsy") afflicts thousands of individuals worldwide, many of them children. It is characterized by nonconvulsive seizures that include a loss of consciousness, accompanied by glassy-eyed staring and bilateral 3 Hz "spike-and-wave" EEG discharges (SWDs). These seizures are brief (5-20 sec) but can occur up to 200 times per day. Approximately ⅓ of subjects are resistant to standard antiabsence drug therapies, and some existing putative therapies have been shown to exacerbate seizures.

Absence seizures involve pathological reverberations between the thalamus and cortex of the brain. A variety of animal models of absence epilepsy exist, and have identified numerous contributing alterations in the function of neuronal ion channels, or mutations in ion channel genes. Most of these alterations, and most current drug therapies, involve voltage-gated calcium and sodium channels. However, recently several neurotransmitter-activated ion channel systems have also been implicated in absence seizures, including the receptor for gamma-aminobutyric acid (GABA).

The "$GABA_A$ receptor" is actually a family of protein complexes expressed at nearly half of the synapses in the central nervous system, and is the main receptor that mediates synaptic inhibition. In addition, GABA receptors are also located extrasynaptically, where they mediate nonsynaptic (also known as tonic) inhibition. The receptor is the primary target of nearly all general anesthetics (e.g., barbiturates, halothane, propofol) and many sedatives (e.g., Valium®, Ambien®), that all bind to the receptor and enhance its function. In contrast, mutations or poisoning of the receptor typically leads to seizures. Thus, the receptor is a prime candidate for pharmacological targeting of antiepileptic medications.

In particular, the drug ganaxolone selectively enhances tonic inhibition mediated by a specific subtype of $GABA_A$ receptor. Although some studies suggest that ganaxolone may be considered for use in treating absence seizures, most reports suggest otherwise. For example, it was recently found, in several rodent models of absence epilepsy, that seizures were associated with increases in $GABA_A$ receptor-mediated tonic inhibition. One group concluded that absence seizure generation requires increased tonic inhibition. Not surprisingly, in these same animal models, further enhancing GABAergic tonic inhibition exacerbated absence seizures. Similar exacerbation was found in models of pharmacologically-induced absence-like seizures, and the Encyclopedia of Basic Epilepsy Research specifically states that ganaxolone should not be given to subjects with absence epilepsy. Therefore, the current consensus in epilepsy research is that ganaxolone, and drugs with similar mechanisms, are probably unsuitable for treating absence epilepsy.

Several human epilepsies have been traced to mutations in the $GABA_A$ receptor, a pentameric transmembrane protein containing an integral chloride ion channel that regulates action potential generation via shunting or hyperpolarization. The mutation that has received the most study is an arginine-to-glutamine substitution at position 43 of the γ2 subunit (γ2R43Q). Human subjects harboring the γ2R43Q mutation present symptoms from a variety of epileptic phenotypes, the most common being Childhood Absence Epilepsy (CAE) and febrile seizures. γ2R43Q knock-in mice (RQ) display absence seizures and generalized EEG spike-and-wave discharges (SWDs) reminiscent of their human counterparts (see FIG. 6). Absence seizures consist of brief losses of consciousness typically lasting 2-15 seconds, along with bilateral, synchronous 3-Hz spike-and-wave discharges (SWDs). Human subjects with the γ2R43Q mutation show evidence of a hyperexcitable cortex compared to unaffected family members, displaying increased intracortical excitability, decreased intracortical inhibition and increased facilitation in response to paired-pulse stimulation. These findings support the hypothesis that a hyperexcitable cortical condition contributes to SWDs in these subjects. A similar "cortical focus theory" for absence seizures was proposed after SWD generation was localized to the somatosensory cortex in a different mouse model. The exact origin of SWDs in γ2R43Q human subjects has not been identified.

The functional effects of the γ2R43Q mutation have been studied in heterologous expression systems (oocytes, HEK293 and COS7 cells), but have led to conflicting results. On one hand, the γ2R43Q mutation has been shown to alter receptor function by slowing receptor deactivation, enhancing desensitization, and reducing benzodiazapine sensitivity. However, others have observed little effect on receptor function. In contrast, several studies agree that the mutation alters $GABA_A$ receptor assembly, trafficking or surface expression. Interestingly, this mutation in the γ2 subunit appears to also affect trafficking of other subunits including α1, α3, β3, β3, and α5. The levels and/or membrane surface expression of the subunits that participate in extrasynaptic tonic inhibition in cortex (α5) and thalamus (α4 and δ) are decreased by the γ2R43Q mutation.

Tonic inhibition has recently been linked to SWD generation and absence seizures. Multiple rodent models of absence epilepsy (GAERS, stargazer, lethargic, tottering) display increases in thalamic inhibitory tonic current, and selective activation of this current produces SWDs and absence seizures in rats. To understand how altered thalamic inhibitory tonic currents could produce SWDs, the anatomy and functional connectivity of neurons in the thalamocortical network must be considered.

Thalamic relay neurons can fire in distinct 'tonic' and 'burst' modes. The tonic firing mode occurs when the membrane is steadily depolarized, and consists of classical sodium channel-dependent action potentials. The burst firing mode, in comparison, occurs when the membrane is hyperpolarized such that T-type voltage-gated calcium channels are allowed to recover from inactivation. A subsequent depolarization then results in a high frequency burst of sodium channel-dependent action potentials riding atop a calcium channel-dependent plateau potential. Thus, increased hyperpolarizing tonic inhibition may shift thalamic relay neurons into the burst firing mode, which may increase the drive onto GABAergic thalamic reticular nucleus (TRN) neurons. In turn, TRN neurons transmit hyperpolarizing IPSPs (inhibitory postsynaptic potentials) back onto thalamic relay neurons, further promoting relay neuron burst firing. This reverberation between relay and TRN neurons is critical for sustaining SWDs. Indeed, even in studies supporting a cortical origin of SWDs, seizure activity spread to the thalamus within a few hundred milliseconds, consistent with the idea that robust absence seizures are a product of the full thalamocortical network.

As shown herein using thalamocortical slices, tonic inhibition is abolished in layer II/III neurons of somatosensory cortex and relay neurons of ventrobasal thalamus of RQ mice. Through Western blotting and voltage-clamp electrophysiology, it was shown that the loss of tonic inhibition is accompanied by altered expression or trafficking of the $GABA_A$ receptor subunits responsible for mediating tonic currents in these areas. Using multielectrode arrays, it was further shown that loss of tonic inhibition increases cortical firing rates, but decreases bursting throughout the thalamocortical circuit, consistent with a depolarization of thalamic relay neurons that shifts them away from the burst firing mode. Selective pharmacological blockade of cortical tonic current in wild type (RR) slices also increases cortical firing rates, paralleling the increased cortical firing in RQ slices, and consistent with the increased cortical excitability observed in γ2R43Q human subjects. Together these results suggest that the combined loss of cortical and thalamic tonic inhibition in RQ mice enhances susceptibility to absence seizures.

Recently a link has been established between tonic inhibition and absence-associated SWD generation, though thus far this link has been associated with only thalamic neurons. Research shows the increase of GABAergic tonic currents in thalamic relay neurons is 'sufficient' to produce SWDs in wild-type rats, and multiple rodent models of absence epilepsy (GAERS, stargazer, lethargic, tottering) express increases in thalamic inhibitory tonic currents. The studies presented herein expand this link to now include cortical neurons. Using continuous in vivo EEG monitoring and pharmacology to selectively manipulate cortical tonic inhibition levels, it is shown that decreasing cortical inhibitory tonic currents is also 'sufficient' to produce SWDs in wild-type (RR) mice, and rescuing the lost cortical tonic currents in RQ mice suppresses SWD expression.

In one aspect, a method of treating absence epilepsy in a subject in need thereof comprises administering ganaxolone in an amount of 0.2 to 2 mg/kg per dose, wherein the subject has been diagnosed with absence epilepsy. As used herein, the term dose refers to a single administration of drug. In general, a dose is not repeated more than once every 3 to four hours, such that up to 6 or even 8 doses can be administered in a day. Dosing can be accomplished less frequently if controlled-release dosing is employed. In an aspect, the subject is a mammalian subject such as a human subject, specifically a human pediatric patient. Non-human mammalian subjects include dogs and livestock animals. In an aspect, the subject suffers from nonconvulsive seizures associated with loss of consciousness, glassy-eyed staring, spike and wave EEG discharges, or a combination thereof. In another aspect, the subject is resistant to standard antiabsence drug therapy. Standard antiabsence drug therapy includes ethosuximide, sodium valproate and lamotrigine, and combinations thereof.

In an aspect, the subject is a pediatric subject. In an aspect, a pediatric subject with absence epilepsy is 1 to 18 years of age, and has an average weight of 10 to 80 kg. Thus, the dose range of ganaxolone is 2 to 160 mg per dose. In an aspect, a pediatric subject with absence epilepsy is 1 to 12 years of age and has a weight of 10 to 50 kg. In this subject population, the dose of ganaxolone is 2 to 100 mg of ganaxolone per administration. In another aspect, a pediatric subject with absence epilepsy is 4 to 12 years of age and has a weight of 15 to 50 kg. In this subject population, the dose of ganaxolone is 3 to 100 mg of ganaxolone per administration.

As described, for example in U.S. Pat. No. 8,618,087, typical dosage forms of ganaxolone contain at least 200 mg of ganaxolone. A dose of as much as 36 mg/kg/day has been used in the treatment of infantile spasms, while doses of 1875 mg/day have been used for treatment of complex partial seizures in adults. Thus, in general, the dosages of ganaxolone typically used to treat seizures are high, sometimes exceeding 1 g per day. Without being held to theory, it is believed that the typically high doses of ganaxolone that have been used previously led to the incorrect conclusion that ganaxolone is not useful for the treatment of absence epilepsy. Specifically, it is proposed that low doses of ganaxolone rescue tonic inhibition, while large doses of ganaxolone over activate tonic inhibition above healthy levels, resulting in reduced efficacy or negative side effects.

In one aspect, the pediatric subject diagnosed with absence epilepsy has a deficit in tonic inhibition. Absence epilepsy can be associated with either an increase or a decrease in tonic inhibition. In the case of absence epilepsy with an increase in tonic inhibition, a further increase in tonic inhibition would be either ineffective or counterproductive. In the case of subjects with a deficit in tonic inhibition, it is expected that ganaxolone can provide a pharmacological rescue of the missing inhibition and alleviate absence seizures. Given the high rate of insensitivity of subjects to standard epilepsy treatments, it is predicted that as many as ⅓ of absence epilepsy subjects may suffer from a deficit in tonic inhibition and could benefit from low dose ganaxolone therapy.

In an aspect, the method further comprises determining that the subject with absence epilepsy is responsive to ganaxolone therapy. In one aspect, determining that a subject is responsive to ganaxolone therapy consists of genetic testing to determine whether mutations or single nucleotide polymorphisms are present in genes for $GABA_A$ receptor subunits that participate in tonic inhibition (e.g., α4, α5 and δ). In an aspect, determining that a subject is responsive to ganaxolone therapy comprises standard clinical practice of precipitating a seizure in the subject, administering a test dose of ganaxolone to the subject, and determining if the subject becomes less susceptible to precipitating further seizures.

In addition, further analysis of the results for treatment of RQ mice with ganaxolone show that low dose ganaxolone can also be used as a sleep aid to treat individuals with sleep disorders. Sleep disruption is a trigger for seizures, and epileptic patients often have sleep disorders, suggesting a "vicious cycle" of interactions between sleep and epilepsy. Absence epilepsy is especially interesting because, like sleep, it involves a) loss of consciousness without convulsions, and b) reverberations between the thalamus and cortex, both of which areas express delta subunit-containing $GABA_A$ receptors that can be manipulated using low-dose ganaxolone.

Specifically, patients with absence epilepsy are known to suffer from disrupted sleep. It was shown in the RQ mouse model that low dose ganaxolone reduces sleep alterations. Without being held to theory, it is believed that thalamocortical function is disrupted in both absence epilepsy and sleep disturbance and that because ganaxolone restores normal thalamocortical function, it can be used to treat both absence epilepsy and sleep disorders. Low dose ganaxolone can be administered to any individual in need of treatment for a sleep disorder, and specifically to patients with absence epilepsy.

Sleep is a state of brain activity defined as unconsciousness from which a person can be aroused by sensory or other stimuli. While asleep, a person undergoes two alternating states of sleep, rapid eye movement (REM) sleep and non-REM (NREM) sleep. NREM sleep is comprised of four sleep stages. Stage 1 (S1) is a state of drowsiness or transition between wake and sleep in which changes that permit slow-wave activity to occur. Stage 2 (S2) is a state of light sleep and the beginning of slow-wave activity (defined as large amplitude rhythm in the delta 0.5-4 Hz frequency band on the EEG). Stage 3 (S3) is entered as sleep becomes deeper and exhibits an increase in slow-wave activity. Stage 4 (S4) is characterized by very deep sleep. REM sleep occurs about 80 to 100 minutes after falling asleep, and is characterized by high frequency EEG activity, bursts of rapid eye movement, and heightened autonomic activity. Sleep progresses in a cycle from stage 1 through stage 4 to REM sleep. A person typically experiences four to six REM periods per sleep period.

One way to assess the efficacy of a sleep aid is to determine the effect of the sleep aid on sleep quality. Sleep quality can be quantified as the intensity of sleep, duration of time to fall asleep, number of arousals from sleep such as the number of brief awakenings, duration of time in slow-wave sleep periods, and/or duration of sleep cycles. The intensity of sleep can be measured by the electroencephalographic slow-wave activity. Brief awakenings are arousals of less than about 1 minute that can contribute to excessive daytime sleepiness. While there is significant variability from person to person, the intensity of slow wave EEG power and the number of brief awakenings, are generally good markers for "good sleep". Specifically, high intensity delta power and few brief awakenings appear to correlate well with the subjective perception of "good sleep"

As used herein, sleep disorders include insomnia, narcolepsy, daytime sleepiness, restless limb syndrome, periodic limb movements, sleep apnea, and snoring.

In one aspect, a method of treating sleep disruptions in a human subject in need thereof comprises administering ganaxolone to the human subject in an amount of 0.2 to 2 mg/kg per dose. In one aspect, the human patient suffers from disrupted sleep due to epilepsy, such as absence epilepsy. In another aspect, the human individual suffers from a sleep disorder. In one aspect, administration of ganaxolone restores durations of non-REM and intensity of slow wave activity toward normal levels. In another aspect, administration of ganaxolone is expected to reduce the number of brief awakenings, improves the REM/non-REM sleep cycle, or both.

Ganaxolone can be prepared, for example, by the methods of U.S. Pat. Nos. 5,319,115 and 8,362,286.

As used herein, "pharmaceutical composition" means therapeutically effective amounts of the compound together with a pharmaceutically acceptable excipient, such as diluents, preservatives, solubilizers, emulsifiers, and adjuvants. As used herein "pharmaceutically acceptable excipients" are well known to those skilled in the art.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents. Although oral administration of ganaxolone is the preferred method, ganaxolone can also be effectively administered subcutaneously.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

In one aspect, a ganaxolone solid or liquid dosage form contains ganaxolone particles with a small molecule complexing agent as described in U.S. Pat. No. 8,618,087, incorporated herein by reference for its disclosure of ganaxolone formulations. Specifically, the ganaxolone particles have a D50 particle size of less than 500 nm. In one aspect, the particles include 50 wt % or greater of ganaxolone. The particles can be formed by known methods such as milling, including wet or dry milling, homogenization, supercritical fluid fracture and precipitation. Such dosage forms can contain an immediate release component and a delayed release component. When in the form of a liquid dosage form, the particles can be in the form of an aqueous dispersion containing, for example, a hydrophilic polymer and a wetting agent as described in U.S. Pat. No. 8,318,714.

Complexing agents are molecules which when added to a small particle composition (D50 of about 75 to about 400 nm, for example) under the appropriate conditions will act as a stabilizing agent. Complexing agents include small compounds under molecular weight 550, which do not contain a sulfonic acid or sulfonic acid/inorganic salt counterion group at the end of an alkyl chain containing more than one saturated carbon atom bonded to the carbon atom bearing the sulfonic acid moiety. Complexing agents include, but are not limited to, phenols and phenolic salts, aromatic acids and esters, carboxylic acids and salts and esters thereof, inorganic acids and bases and amino acids and esters and salts thereof. Some examples include but are not limited to phenol, methylparaben, propylparaben, potassium methylparaben, sodium methylparaben, BHT, sorbic acid, ascorbic acid, p-aminobenzoic acid, benzoic acid ascorbic acid, methyl anthranilate, anthranilic acid, picolinic acids and alkyl esters thereof, and sodium benzoate.

The invention is further illustrated by the following non-limiting examples.

EXAMPLES

Methods

Whole-Cell Patch Clamp Experiments

Horizontal slices (400 μm) were prepared from the brains of C57BL/6J mice RR and RQ mice of either sex (16-26 days old). All procedures were approved by the University of Wisconsin Institutional Animal Care and Use Committee. Mice were anesthetized with isoflurane, decapitated, and the brain was removed and placed in ice-cold cutting solution containing (in mM): 125 NaCl, 25 NaHCO$_3$, 2.5 KCl, 1.25 NaH$_2$PO$_4$, 0.5 CaCl$_2$, 3.35 MgCl$_2$, 25 D-Glucose, 13.87 M sucrose, and bubbled with 95% O$_2$ and 5% CO$_2$. Slices were cut using a vibratome (Leica VT 10005, Global Medical Imaging; Ramsey, Minn.) and placed in an incubation chamber containing standard 2 mM CaCl$_2$, 1 mM MgCl$_2$ artificial cerebrospinal fluid (ACSF) at room temperature for 1 hour before being used for recordings. Whole cell patch-clamp recordings were made from somatosensory cortical layer II/III pyramidal cells or ventrobasal thalamic relay cells, visualized using an upright differential interference contrast microscope (Axioskop FS2, Zeiss; Oberkochen, Germany). Patch pipettes were pulled from thin-walled borosilicate glass (World Precision Instruments; Sarasota, Fla.) with a resistance of 3-5 MΩ when filled with intracellular solution containing (in mM): 140 K-gluconate, 10 EGTA, 10 HEPES, 20 phosphocreatine, 2 Mg$_2$ATP, 0.3 NaGTP (pH 7.3, 310 mOsm). Recordings were made in a submerged chamber at room temperature using a MultiClamp 700B amplifier (Axon Instruments; Foster City, Calif.), filtered at 4 kHz and digitized at 10 kHz using a Digidata 1322A analog-digital interface (Axon Instruments). Data were acquired to a Macintosh G4 (Apple Computer; Cupertino, Calif.) using Axograph X v1.1.4 (Molecular Devices; Sunnyvale, Calif.).

Data segments (120 s) prior to bath application of bicuculline (100 μM) were analyzed for miniature inhibitory postsynaptic currents (mIPSCs), using the variable amplitude template-matching algorithm in Axograph ($\tau_1$=0.64 msec, $\tau_2$=14.95 msec).

Additional segments (30 s) just prior to and 90 s after bicuculline administration were analyzed to quantify inhibitory tonic currents. All-point amplitude histograms were computed for each segment, and fit with a Gaussian function only to the outward current portions relative to the peak in order to omit components arising from inward phasic mIPSCs. Tonic current was calculated as the difference between the fitted Gaussian means before and after bicuculline administration. Current density (pA/pF) was calculated by dividing the current by cell capacitance. Similar fitting was used to measure the currents produced by THIP (4,5,6,7-tetrahydroisoxazolo[5,4-c]pyridin-3-ol; Gaboxadol), allopregnanolone (ALLO) and ganaxolone (GANX).

Multichannel Electrode Array Recordings

Thalamocortical slices (400 μm) were prepared as above and placed on an interface chamber perfused with 3-5 ml/min of low-Mg$^{2+}$ (200 μM) ACSF. Two to four 16-channel arrays (4×4, NeuroNexus; Ann Arbor, Mich.) were inserted into somatosensory cortex or ventrobasal thalamus. Data were acquired continuously using Tucker-Davis Technologies (TDT) SH16 headstages, Medusa preamplifiers, and RX5 Pentusa Base Station (TDT; Alachua, Fla.) at a 12.2 kHz sampling frequency. Spikes were detected as events larger than 2.5 standard deviations above baseline noise, with 5 millisecond segments surrounding each spike captured for analysis. Spikes were sorted by principal component analysis of spike waveforms, followed by clustering of waveforms projected into the space spanned by the first three principal components using the Klustakwik algorithm. Homewritten Matlab® (MathWorks®, Natick, N.J.) code was used to analyze firing and bursting of each neuron, based on the timestamps of the sorted spikes. 'Generic' bursts were defined to reflect any tendency to fire in groups of spikes, and were detected as groups of spikes separated from other groups by gaps of ≥50 msec. We also used a measure specifically reflecting the expected statistics of thalamic neuron bursting mediated by T-type calcium channels ('T-bursts'), which were detected as events with an interburst gap of ≥100 msec combined with an intraburst gap of ≤8 msec. The 'burst fraction' in both cases was computed as the number of bursts containing 2 or more spikes divided by the total number of bursts.

Subcellular Fractionation and Western Blotting

To evaluate differences in GABA$_A$ receptor subunit protein expression and trafficking, somatosensory cortex and ventrobasal thalamus were dissected from horizontal slices (1200 μm) prepared as above, and immediately placed on dry ice then stored at −80° C. Samples were thawed and suspended in 50 μL 0.1% Triton buffer with protease inhibitors (Sigma®; St. Louis, Mo.) and further disrupted with 3-5 pumps of a fine-tipped syringe. After 10 minutes at room temperature, samples were centrifuged at 8,000 g for 10 minutes at 4° C. The supernatant (organelle) fraction was then transferred to another chilled tube and the pellet (plasma membrane) fraction was resuspended in 50 μL Triton™ buffer.

A Bradford protein assay (Bio-Rad; Hercules, Calif.) was performed on all samples to quantify protein concentration. Loading buffer was added, samples were boiled, and proteins were one-dimensionally separated on Mini-PROTEAN® TGXT$^M$ (Bio-Rad) gels (10%), then transferred to polyvinylidene difluoride membranes (Immobilon®-P, Millipore; Billerica, Mass.). Membranes were probed with antibodies against GABA$_A$ receptor subunits α1 (#OPA1-04100: Thermo Scientific; Waltham, Mass.), α4 (#AB5459: Millipore), α5 (#AB9678: Millipore), δ (#868-GDN: PhosphoSolutions®; Aurora, Colo.), and γ2 (#OPA1-04111: Thermo Scientific). Actin (#691001: MP Biomedicals; Solon, Ohio) and the endoplasmic reticulum-enriched protein calreticulin (#06-661: Millipore) were also probed and used as loading and organelle fraction controls, respectively. Some gels were stripped with Restore™ PLUS Western Blot Stripping Buffer (Thermo Scientific) and re-blotted for a second protein. Corresponding secondary antibodies (1:20k) (Santa Cruz Biotechnology; Santa Cruz, Calif.) were applied and immunolabeling of membranes was detected via Super-Signal West Femto (Thermo Scientific) chemiluminescence using a UVP ChemiDoc-IT™ Imaging System controlled by Image Acquisition and Analysis software (VisionWorks LS: UVP; Upland, Calif.).

RQ Mice Display SWDs In Vivo.

In human subjects expressing the γ2R43Q mutation, penetrance of the absence epilepsy phenotype depends strongly on genetic background. This dependence also applies to knock-in mice, such that penetrance can vary even between colonies of γ2R43Q mice that are nominally of the same background strain. Thus it is important to correlate the epilepsy phenotype with putative underlying cellular or network mechanisms.

EEG Implantation and Monitoring of SWDs

The present study used wild-type Harlan C57BL/6J-OlaHsd and γ2R43Q knock-in mice bred into a background of C57BL/6J-OlaHsd mice. Behavioral and electrographic markers of absence epilepsy in these animals were confirmed by video-EEG monitoring. In-depth detailing of surgery and electrode implantation are described in the prior art. Briefly, P24 mice were implanted, under isoflurane anesthesia (1%-2% in 100% $O_2$), for chronic EEG recordings with gold plated miniature screw electrodes over the right and left frontal and parietal cortices, and one over the cerebellum as reference. Two vinyl-coated braided stainless steel wire electrodes were placed in the nuchal muscle for electromyogram (EMG) recording of muscle activity. All electrodes were gathered into a flexible cable and connected to the Multichannel Neurophysiology Recording system (Tucker-Davis Technologies, TDT, Alachua, Fla., USA). EEG and EMG signals were collected continuously at a sampling rate of 256 Hz (digitally filtered between 0.1 and 100 Hz). Continuous EEG recordings with occasional video monitoring were made and SWDs were scored off-line Animals were given a 3-day recovery period after surgery before SWD scoring began. A SWD event was defined as a brief (approximately 2 seconds long) approximately 6 Hz signal synchronized across all EEG leads, with a corresponding lack of signal in the EMG lead. Only SWD events that occurred >2 min from slow-wave-sleep periods were used for quantification. SWD event durations were measured from the first synchronized positive peak signal to the last synchronized positive peak within an event. SWD "bouts" were defined as groups of SWD events separated from other events by <30 seconds. Inter-bout-intervals were defined as the time between the beginnings of consecutive bouts.

Drugs and Injection Schedule

Figure 8:
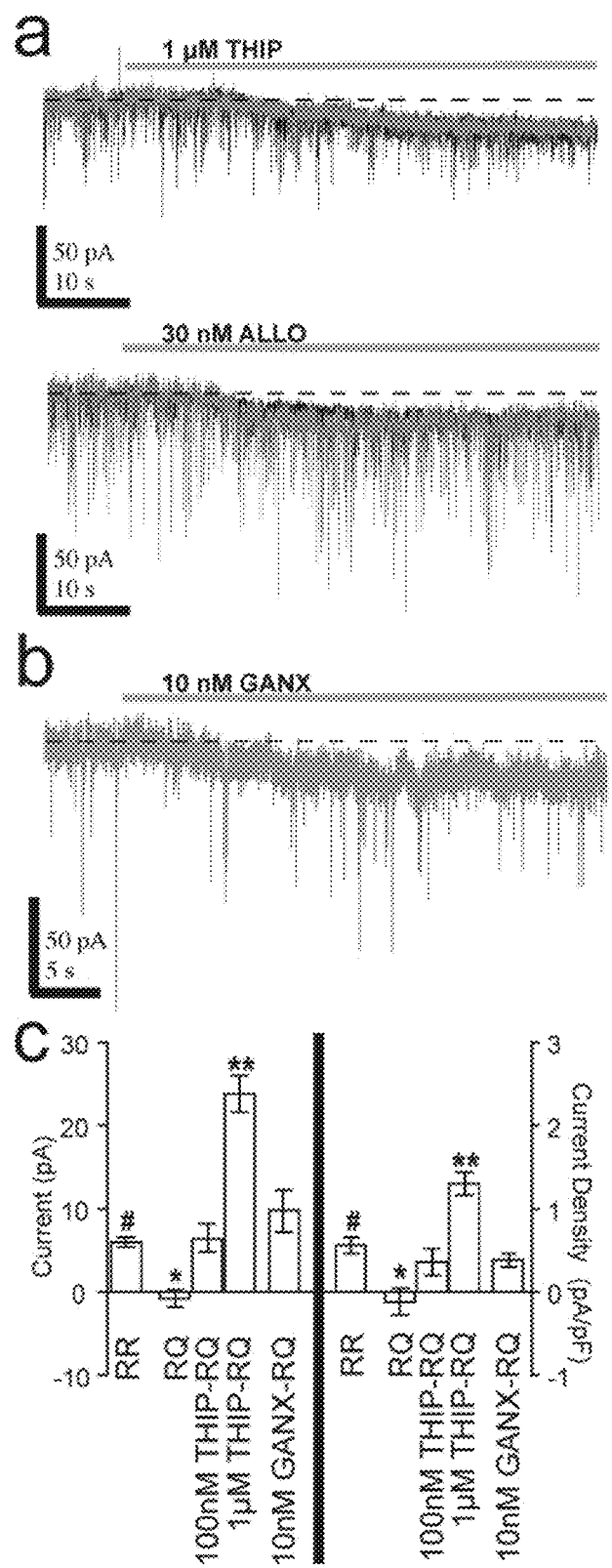
FIG. 8 shows that $GABA_A$ receptor δ-subunit-selective agonists rescue tonic inhibition in principal RQ cortical neurons. Panel a) Example voltage-clamp traces for RR (black-behind) and RQ (grey-front) cortical layer II/III cell recordings during 1 μM THIP (top) and 30 nM allopregnanolone (ALLO: bottom) treatments. Both $GABA_A$ receptor δ-subunit-selective agonist treatments induce indistinguishable current amplitudes and densities in RQ compared to RR. Panel b) Example voltage-clamp trace for RQ cortical layer II/III cell recording during a 10 nM ganaxolone (GANX) treatment also shows an increase in the holding current, similar to THIP and ALLO. Panel c) Tonic current amplitude (left y-axis) and density (right y-axis) quantifications show RR level inhibitory tonic currents can be rescued in RQ with 100 nM THIP and 10 nM GANX treatments, whereas 1 μM THIP treatment in RQ produces 2-4 times more holding current amplitude ($p<0.05$) and density ($p<0.05$) than that seen in RR untreated neurons.
Figure 9:
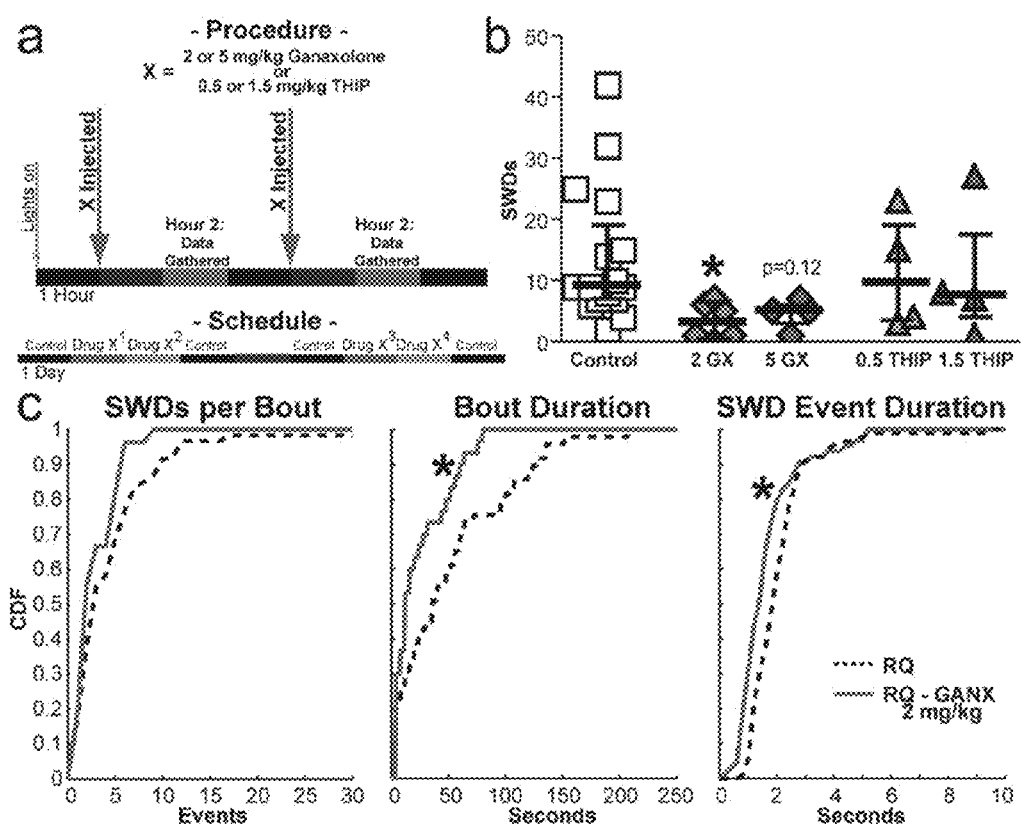
FIG. 9 shows that rescuing cortical tonic inhibition tempers SWDs in RQ mice. Panel a) Schematic depicting administration times and drug schedule investigating 4 drug-treatment conditions in RQ mice. GANX (2 and 5 mg/kg) or THIP (0.5 and 1.5 mg/kg) solutions were i.p. injected in RQ mice twice a day for 4 out of 7 days. Panel b) RQ SWD event quantification during the second hour after drug administration shows the 2 mg/kg GANX ($p<0.05$) treatment decreased SWD expression compared to control hours. Panel c) Cumulative distributions of RQ SWD activity after 2 mg/kg GANX treatment shows that bout ($p<0.05$) and SWD event ($p<0.05$) durations are decreased after treatment.

L655 (L9787), GANX (G7795) and THIP (T101) were all obtained from Sigma® (St. Louis, Mo.). L655 and GANX were dissolved in a 30% DMSO-saline solution, while THIP was dissolved in 100% saline. Mice were intraperitoneally (i.p.) injected with 2 mg/kg doses of L655, 2 and 5 mg/kg doses of GANX, or 0.5 and 1.5 mg/kg doses of THIP. Drug solutions were concentrated so 160 uL of solution was injected for each injection. L655 was administered to RR mice 2 and 4 hours after lights out (FIG. 8) for 2 consecutive days beginning 5 days after surgery. These mice were not injected for the subsequent 2 days, but were given vehicle injections on day 9. Ganaxolone or THIP injections were administered to RQ mice 1 and 4 hours after lights out (FIG. 9). Drug injections for RQ mice began on day 5 after surgery and consisted of 2 injections of one drug and dose, with a different drug and dose for days 6, 10, and 11. No injections were given to RQ mice on days 7-9.

Statistics

When comparing normally distributed data, two groups were assessed with a t-test and comparisons of three or more were assessed with ANOVA. When comparing non-normally distributed data, a Kruskal-Wallis examination of medians was used to compare multiple groups.

Evaluation of Sleep Patterns

RR and RQ mice (n=3 each) were monitored with video and EEG recordings. After a baseline recording period of 3 days to evaluate sleep patterns, the RQ mice were injected with GANX (2 mg/kg i.p.) on two consecutive days. Sleep stages (Wake, NREM and REM) were scored visually from the EEG by an experienced scorer. For statistical analysis, EEG delta power (0.5-4 Hz) was normalized by dividing by the sum of power in the non-delta bands (6-100 Hz).

Example 1

Synaptic Inhibition is Reduced in RQ Thalamus and Cortex

The RQ mutation hinders $GABA_A$ receptor assembly, trafficking and surface expression, and decreases cortical mIPSC amplitude in RQ mice. The present analysis of mIPSCs corroborated the latter finding, showing a decrease (31%) in mIPSC amplitude in somatosensory cortical layer II/III neurons (pA: mean±SEM, N; RR: 26.2±2.9, 9; RQ: 18.1±1.4, 8, p<0.05; FIG. 1, panel a and panel b) and also a decrease (34%) in thalamic relay neurons (RR: 41.1±4.8, 9; RQ: 27.1±2.1, 7, p<0.05; FIG. 1, panel d and panel e) mIPSC frequency was unaffected in both areas (FIG. 1, panel c and panel f). Weighted decay time-constants for cortical layer II/III neurons are not different for RQ (ms: mean±SEM, N; 24.0±1.6, 4) compared to RR (19.0±2.2, 5), but are increased for RQ thalamic neurons compared to RR (RR: 8.5±0.8, 7; RQ: 13.8±0.6, 5, p<0.001) (data not shown).

Example 2

GABAergic Tonic Inhibition is Abolished in RQ Cortical and Thalamic Neurons

Figure 2:
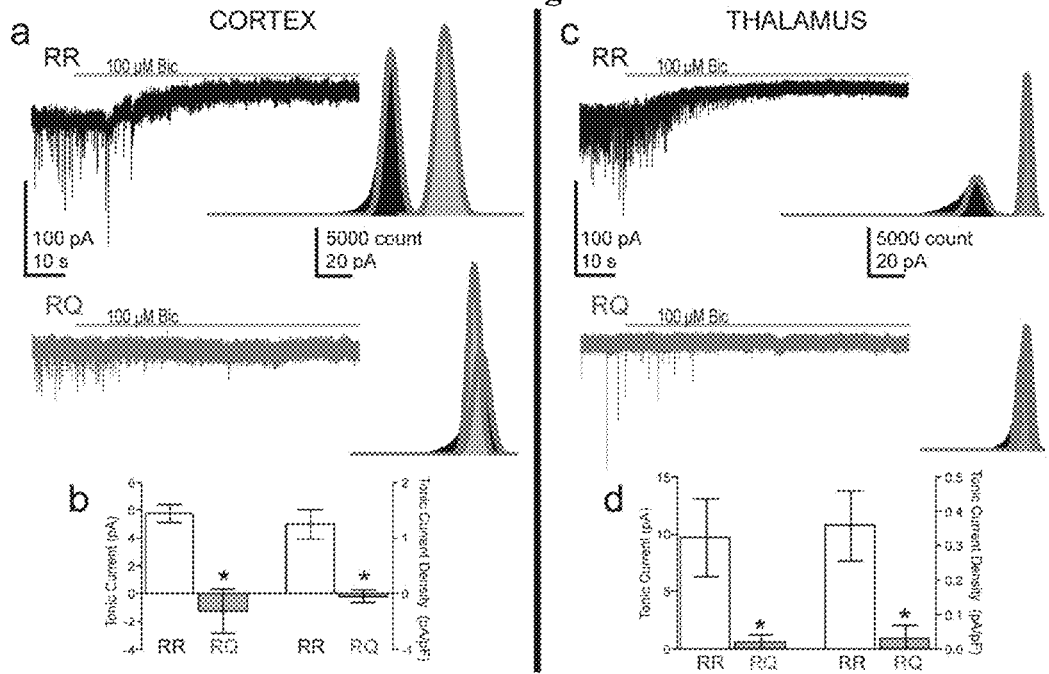
FIG. 2 shows that tonic currents are abolished in RQ mouse cortex and thalamus. Panel a) Example voltage-clamp traces for RR (above: black) and RQ (below: grey) cortical layer II/III cell recordings during 100 μM Bicuculline administration (grey bars). Insets) Corresponding all-points amplitude histograms for data before (black) and after (grey) bicuculline administration. Histograms were fit with a Gaussian function (dark grey) only on the right side of the distribution, thus omitting components due to phasic mIPSCs. Panel b) Tonic current amplitude (pA) (left axis) and tonic current density (pA/pF) (right axis) are abolished in RQ cortical cells ($p<0.05$) compared to control. Panels c-d) Same as a-b, but for ventrobasal thalamic relay neurons.

Although reductions in synaptic inhibition are a potential mechanism for hyperexceitability and absence epilepsy in the RQ mice, the γ2R43Q mutation may affect other processes as well. For example, based on studies in transfected cultured neurons, it has been proposed that this mutation may contribute to absence epilepsy by reducing tonic inhibition. Therefore, to directly test this hypothesis in an animal model, tonic inhibition in slices from RR and RQ knock-in mice was examined. Using whole cell voltage clamp recordings it was found that, whereas RR neurons exhibit a substantial inhibitory tonic current, this current was entirely abolished in RQ mutant somatosensory cortical layer II/III neurons (pA: mean±SEM, N; RR: 5.8±0.6, 5; RQ: −1.2±1.6, 4, p<0.05; FIG. 2, panels a and b), as well as in thalamic relay neurons (RR 10.6±3.6, 9; RQ: 0.6±0.7, 6, p<0.05; FIG. 2, panels c and d).

Example 3

$GABA_A$ Receptor Function or Expression is Altered in a Region-Specific Manner

Figure 3:
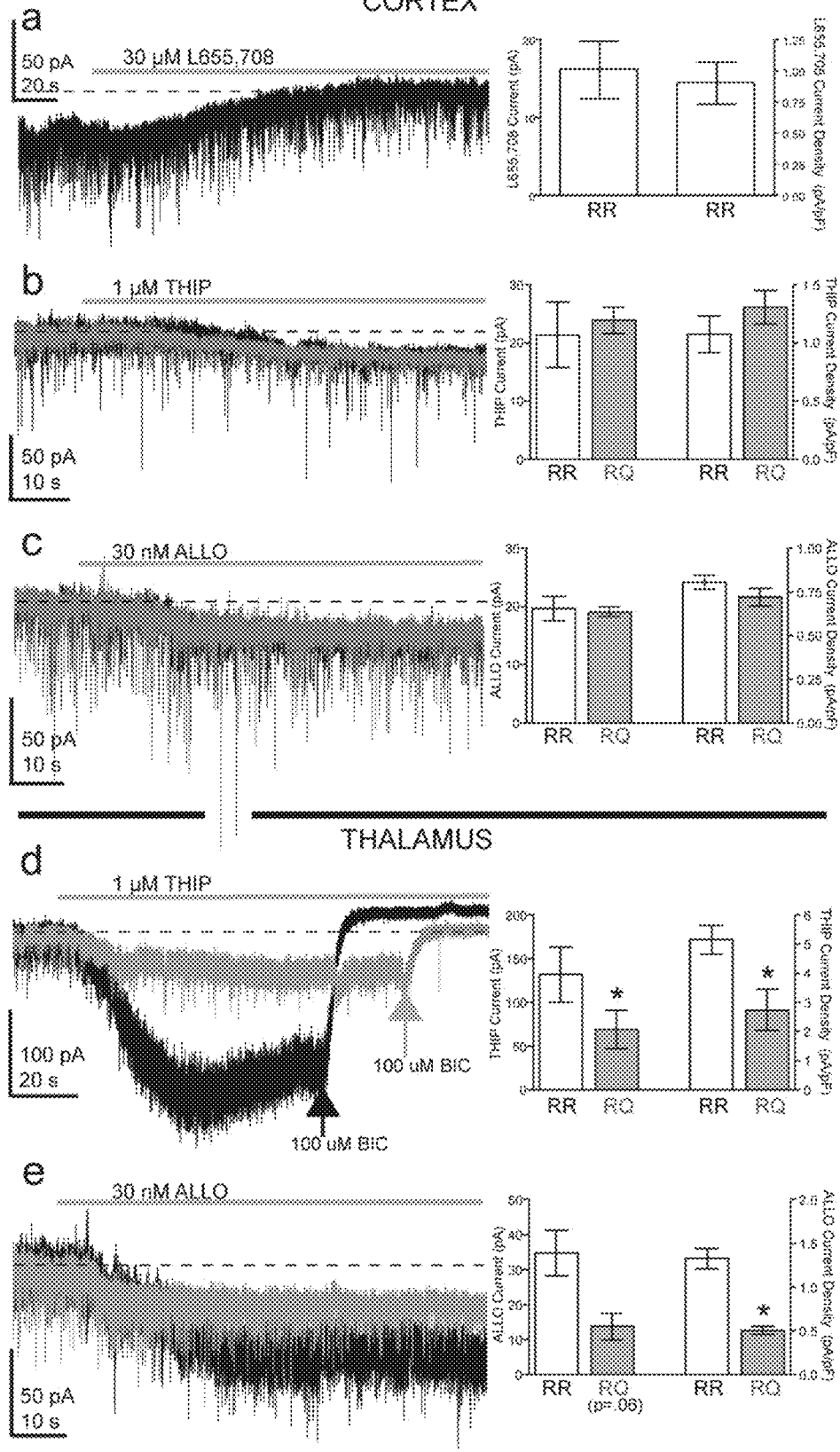
FIG. 3 shows that RQ mice display region-specific and subunit-specific changes in tonic inhibition. Panel a) Example voltage-clamp traces for RR cortical layer II/III cell recordings during 30 μM L655,708 administration (grey bar). The current density blocked by L655,708 is not significantly different than that blocked by bicuculline (see FIG. 2). Panel b) Both THIP (4,5,6,7-tetrahydroisoxazolo [5,4-c]pyridin-3-ol) (1 μM) and panel c) allopregnanolone (ALLO; 30 nM) induce indistinguishable current amplitude and density in RQ (grey traces) compared to RR (black traces). Panel d) In thalamic relay neurons, however, THIP- and panel e) ALLO-induced current densities are significantly reduced in RQ compared to RR (approximately 50%; $p<0.05$).

The tonic current in RR somatosensory cortical layer II/III cells (FIG. 2, panel a) was completely blocked by the α5 subunit-selective inverse agonist L655,708 (30 μM; FIG. 3, panel a), matching previous studies showing that the α5 subunit is responsible for most or all of the native tonic inhibition in these neurons. Thus the loss of cortical tonic inhibition in RQ mice may involve reduced expression or function of the α5 subunit.

In contrast, application of the agonist THIP (1 μM, a concentration previously shown to be selective for δ subunit-containing receptors) evoked currents of similar magnitude in RR and RQ cortical neurons (pA, N; RR: 21.4±5.7, 4; RQ: 23.8±2.2, 5; p=0.67; FIG. 3, panel b). A similar profile of effects was observed with allopregnanolone (30 nM; FIG. 3, panel c), a neurosteroid that also selectively activates δ subunit-containing receptors. Together, these results suggest that receptors containing the δ subunit are present in cortical neurons, and can be recruited by both exogenous drugs and endogenous modulators, potentially providing pharmacological avenues to rescue cortical tonic inhibition in cases where it has been genetically compromised.

In contrast to cortical layer II/III neurons, thalamic relay neurons rely solely on δ subunit-containing $GABA_A$ receptors to produce inhibitory tonic currents. RQ thalamic neurons responded to THIP with 47% of the current produced in RR thalamic neurons (pA, N; RR: 131.7±31.2, 5; RQ: 69.3±22.4, 4, p<0.05; FIG. 3, panel d). Similarly, in RQ thalamic neurons, allopregnanolone produced 39% of the current observed in RR (pA, N; RR: 34.7±6.5, 5; RQ: 13.7±3.8, 3, p<0.05; FIG. 3, panel e). These results suggest that δ subunit-containing $GABA_A$ receptors are either expressed at lower levels, or have reduced activation, in thalamic relay neurons of RQ mice compared to RR mice.

Example 4

Figure 4:
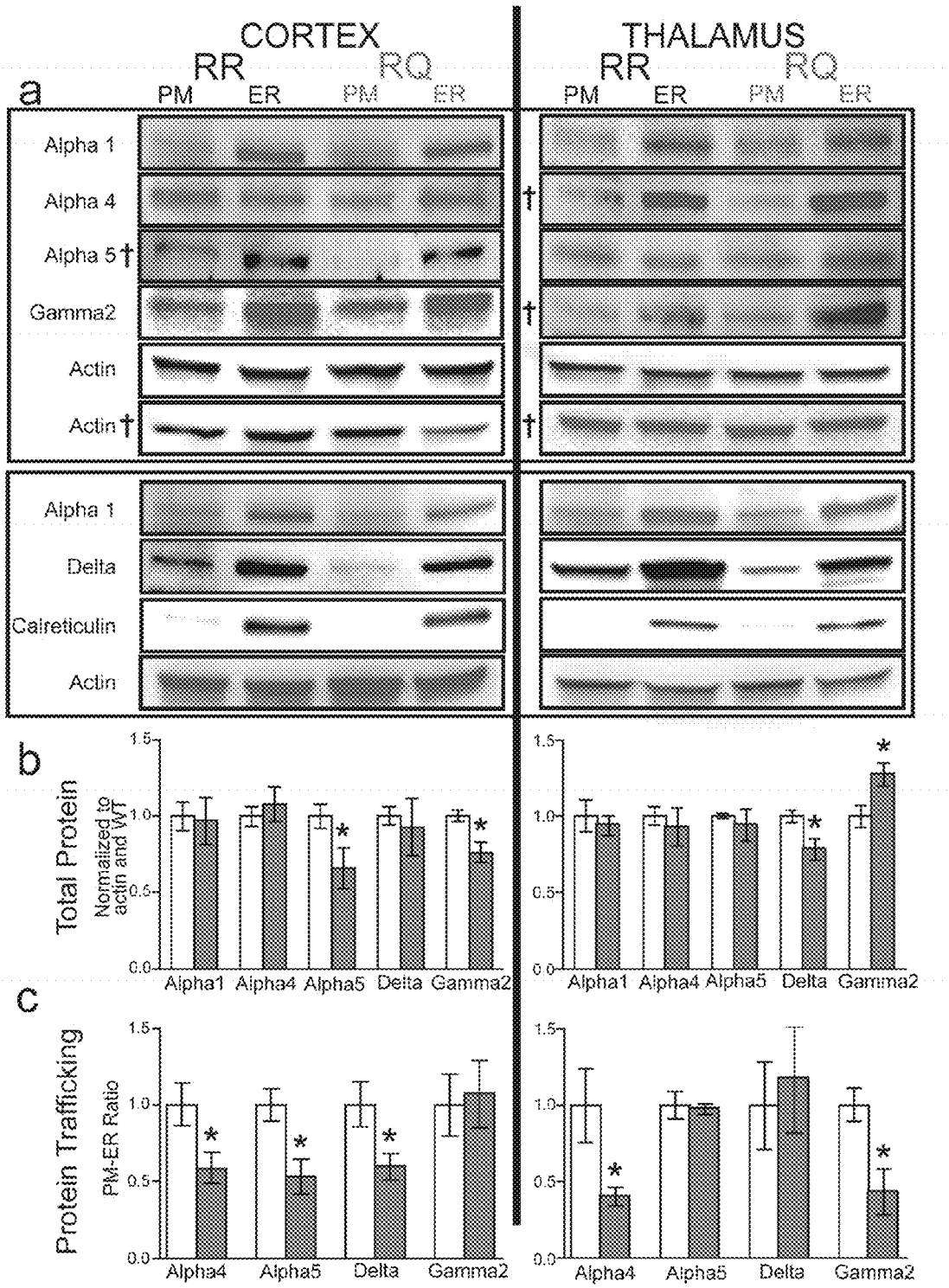
FIG. 4 shows that $GABA_A$ receptor subunit trafficking is altered in a region-specific manner. Panel a) Western Blots for 5 $GABA_A$ receptor subunits for RR and RQ mouse plasma membrane (PM) and intracellular organelle (ER) fractions. Calreticulin (a marker for endoplasmic reticulum) and actin were used as controls for fraction specificity and loading quantity, respectively. The crosses denote probes that were run on a second set of gels, to avoid interference with incompletely stripped lanes from the first set of gels. Panel b) Measures of total protein (PM+ER) display decreases in α5- and γ2-subunit ($p<0.05$) levels in RQ cortex (grey bars) and a decrease in δ-subunit ($p<0.05$) in RQ thalamus compared to RR (white bars). Panel c) Protein trafficking to the cell surface (evaluated as the PM/ER ratio) was also reduced for the α4-, α5- and δ-subunits in the cortex ($p<0.05$). In thalamus, trafficking to the surface was reduced for the γ2-subunit ($p<0.05$). Although δ subunit trafficking in the thalamus was not reduced, there was a reduction in trafficking of the α4 subunit ($p<0.05$), the obligatory partner for δ subunit-mediated tonic currents in thalamus.

Expression of $GABA_A$ Receptor Subunit Proteins Involved in Tonic Inhibition is Reduced in RQ Neurons To test whether the loss of tonic inhibition in cortical and thalamic neurons was related to changes in the $GABA_A$ receptor subunit proteins involved in tonic inhibition, we examined the levels of these proteins in whole tissue subcellular fractions (plasma membrane (PM) and intracellular organelles (ER)) using Western blotting. The 'total protein' (PM+ER) and 'surface trafficking' (PM/ER) levels were calculated for all proteins assessed (α1, α4, α5, γ2, and δ). Surface trafficking was further normalized to al-trafficking levels because previous research showed that the R43Q mutation did not alter al membrane trafficking. The RQ somatosensory cortex showed a marked decrease in total α5 subunit protein expression (fraction of RR expression, N) (0.66±0.14, 8, p<0.05), as well as a decrease in total γ2 subunit expression (0.76±0.07, 4, p<0.05; FIG. 4, panel b). Membrane surface trafficking was also reduced for the α4 (RQ: 0.59±0.10, 8. P<0.05), α5 (RQ: 0.53±0.11, 6, p<0.05), and 6 (RQ: 0.60±0.09, 6, p<0.05) (FIG. 4, panel b) subunit proteins. Thus, the loss of cortical tonic inhibition we observed is consistent with the reduced expression of α5 subunits in cortical neuronal surface membranes.

In contrast to the cortex, thalamic tonic inhibition is mediated by receptors containing the obligatory pairing of $GABA_A$ receptor α4 and δ subunits. RQ thalamus showed a reduction in total δ subunit protein levels (0.78±0.07, 6, p<0.05; FIG. 4, panel b). Although a reduction in the trafficking of thalamic δ subunit protein (1.17±0.35, 4, p=0.72) was not observed, there was a decrease in surface trafficking of α4 subunits (0.40±0.06, 5, p<0.05; FIG. 4, panel c). Unlike RQ somatosensory cortex, RQ thalamus showed an increase in total γ2 subunit levels (1.27±0.08, 6, p<0.05; FIG. 4, panel b), but a decrease in γ2 subunit trafficking to the membrane surface (0.43±0.15, 4, p<0.05; FIG. 4, panel c).

Example 5

Firing Rates and Bursting Behaviors are Altered in RQ Thalamocortical Slices

Figure 5:
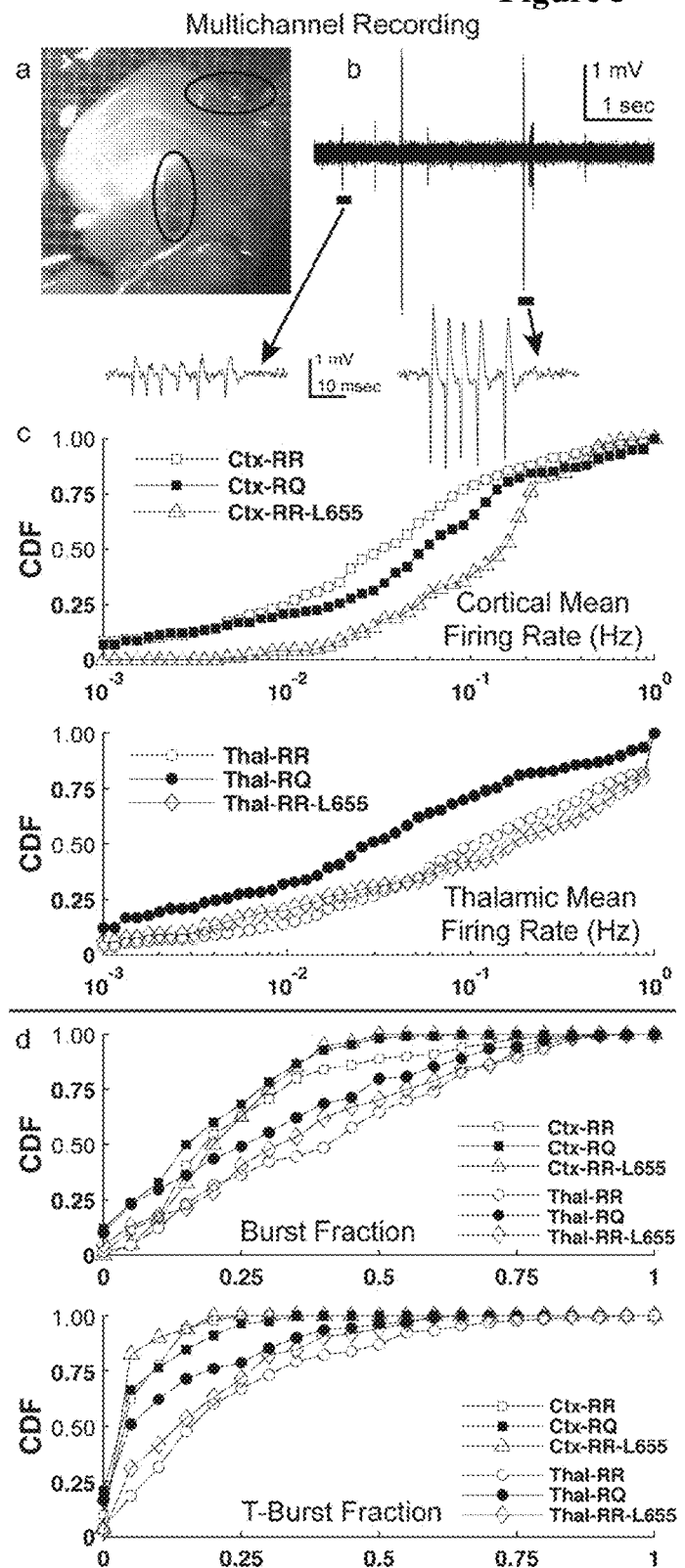
FIG. 5 shows that RQ mouse thalamocortical slices display elevated cortical firing and reduced thalamic bursting. Panel a) A thalamocortical slice with two multielectrode arrays (black ovals) placed in layer II/III cortex (upper) and ventrobasal thalamus (lower). Panel b) Top: A segment of recording from an electrode located in thalamus. Bottom: Expanded segments, corresponding to the black bars in the recording above, and illustrating burst firing of two different neurons (see Methods). Panel c) Cumulative distribution functions (CDF) of mean firing rates for cortex (CTX, upper) and thalamus (Thal, lower), for RR, RQ, and RR in the presence of L655,708 (referred to as L655 or RR-L655). For cortex, both RQ and L655 display increased firing rates compared with RR ($p<0.01$). In thalamus, RQ displays reduced firing rates compared to RR ($p<0.01$), whereas no change is observed for L655. Panel d) CDF plots for generic burst fractions (upper) and T-burst fractions (lower, see Methods). For generic burst fraction, thalamus displayed a higher burst fraction than cortex in all conditions. In thalamus, RQ burst fraction was reduced compared to RR ($p<0.05$), whereas L655 was not. In cortex, neither RQ nor L655 differed from RR. For T-burst fraction, RR thalamus displayed a higher value than RR cortex ($p<0.01$), RQ cortex ($p<0.01$), and RQ thalamus ($p<0.01$), whereas neither RQ area was different than RR cortex.

Although tonic inhibition is known to contribute to neuronal responsiveness, its role in thalamocortical network activity has not been studied in detail. To explore this role, multielectrode extracellular recording arrays were used to examine neuronal spiking and burst firing in somatosensory cortex and ventrobasal thalamus of RR and RQ thalamocortical slices, as well as RR thalamocortical slices treated with L655,708 (30 μM) to selectively block α5 subunit-mediated tonic current in cortical neurons (RR-L655). Cumulative distribution plots of the average firing rates in cortical neurons show increased firing rates for RQ (median rate in Hz, [25:75 percentiles], N cells; p-value (Kruskal-Wallis) (0.06, [0.02:0.14], 230, p<0.01) and RR-L655 (0.17, [0.06:0.22], 96, p<0.01) compared with RR (0.04, [0.01: 0.09], 328; FIG. 5, panel c). Conversely, RQ thalamic neurons displayed decreased firing rates (0.02, [0.00:0.13], 216, p<0.01) compared to RR (0.11, [0.03:0.52], 444), whereas RR-L655 thalamic neurons did not (0.18, [0.02: 0.73], 122; FIG. 5, panel c).

Bursting activity was assessed using two definitions of bursts: i) 'generic' bursts, reflecting any tendency to fire in groups of spikes, and ii) 'T-bursts', reflecting the temporal structure characteristic of thalamic relay neurons firing in burst mode, mediated by T-type calcium channel-dependent plateau potentials (see Methods). The 'burst fraction' quantified the probability that a neuron fired bursts versus lone spikes.

For generic bursts, the cortical burst fraction was lower than the thalamic burst fraction in all conditions (RR: p<0.01; RQ: p<0.05; RR-L655: p<0.05; FIG. 5, panel d). The thalamic burst fraction was reduced in RQ compared to RR, but not in RR-L655 (RR: 0.43, [0.18:0.64], 130; RQ: 0.29, [0.09:0.49], 108, p<0.05; RR-L655:0.35[0.20:0.59], 84; FIG. 5, panel d). There were no differences observed among cortical burst fractions (RR: 0.21, [0.14:0.34], 99; RQ: 0.18, [0.10:0.32], 110; RR-L655:0.23, [0.16:0.33], 80; FIG. 5, panel d).

Similar to the generic burst fraction, RR cortex had a lower T-burst fraction (0.03, [0.01:0.09], 99, p<0.01) than RR thalamus (0.16, [0.08:0.31], 130, FIG. 5, panel d). Addition of L655,708 to RR slices did not alter the T-burst fraction in either cortex (0.03, [0.02:0.04], 80) or thalamus (0.15, [0.04:0.27], 84) from control. However, the T-burst fraction was reduced in RQ thalamus compared with RR thalamus (0.05, [0.01:0.16], 108, p<0.01; FIG. 5, panel d), but was not significantly different than in RQ-cortex (0.03, [0.00:0.09], 110) compared to control.

Closer examination of T-bursts in RR slices revealed that thalamic neurons displayed more spikes per burst than cortex (cortex: 2, [2:2], 99; thalamus: 2, [2:3], 130; p<0.01); as well as longer burst durations (in ms; cortex: 4.1, [0.6: 5.7], 99; thalamus: 5.1, [3.6:7.9], 130; p<0.01). Neither RQ nor RR-L655 neurons differed from control in the number of spikes per burst (RQ cortex: 2, [2:2], 110; RQ thalamus: 2, [2:3], 108; RR-L655 cortex: 2, [2:2], 80; RR-L655 thalamus: 3, [2:4], 84) or in burst durations (RQ cortex: 3.2, [0.8:6.0], 110; RQ thalamus: 6.4, [2.6:9.1], 108; RR-L655 cortex: 3.6, [1.5:5.2], 80; RR-L655 thalamus: 6.1, [3.5:8.9], 84). Similar to control, thalamus displayed more spikes per burst (p<0.01) and longer T-bursts (p<0.01) than cortex in both RQ and RR-L655.

Discussion of Example 1-5

The major findings are that mice expressing the γ2R43Q mutation entirely lack GABAergic tonic currents in both somatosensory cortical layer II/III pyramidal (FIG. 2, panels a and b) and ventrobasal thalamic relay neurons (FIG. 2, panels c and d), and that these deficiencies increase cortical firing rates (FIG. 5, panel c) and decrease thalamic T-bursting (FIG. 5, panel d). The loss of tonic currents in RQ mice is correlated with decreases in surface trafficking of different $GABA_A$ receptor subunits responsible for generating these currents in cortex and thalamus (FIG. 4). Selective pharmacological blockade of cortical tonic currents increased cortical firing rates as expected, but did not affect thalamic firing rates or bursting behaviors. These results are consistent with the loss of tonic currents causing neuronal depolarization that renders cortical neurons hyperexcitable and shifts thalamic relay neurons away from a burst-firing mode.

Mutation or over-expression of the γ2 subunit of the $GABA_A$ receptor was previously shown to interfere with receptor assembly or trafficking of multiple $GABA_A$-subunits, including the α5 subunit that mediates tonic inhibition in mouse somatosensory cortex and the δ subunit that mediates tonic inhibition in thalamus. The results match with these findings, showing a decrease in membrane trafficking for multiple subunits in the cortex (α4, α5 & δ) and thalamus (α4 & γ2) (FIG. 4), and also complement previous evidence that the R43Q mutation impairs surface expression of functional $GABA_A$ receptors that could result in reduced synaptic inhibition (IPSCs) (FIG. 1). In addition to absence epilepsy, however, this mutation also causes febrile seizures in humans and RQ mice. Thus, the question arises as to whether the observed changes in tonic and phasic inhibition contribute differentially or synergistically to the absence and febrile seizure phenotypes. This issue is complicated somewhat by the variable penetrance of the absence phenotype, even amongst mice that share the C57Bl6 background, possibly due to subtle differences in genetic background between colonies or in rearing conditions. It has recently been shown that C57Bl6 RQ mice that do not display absence seizures continue to express febrile seizures, demonstrating that the two phenotypes are dissociable in the presence of the mutation. The C57Bl6 RQ mice studied here have absence seizures (FIG. 6), have changes in both tonic and phasic inhibition and have altered thalamocortical signaling.

In RR cortical neurons, the α5 subunit-selective inverse agonist L655,708 blocked as much tonic current as did the broad-spectrum $GABA_A$ receptor antagonist bicuculline, confirming that most or all of the active tonic current in these neurons is mediated by α5 subunit-containing receptors. Thus, the loss of tonic current in RQ cortical neurons is consistent with a reduction in protein expression and trafficking of the α5 subunit in RQ, as confirmed by Western blotting (FIG. 4, panels b and c).

RQ thalamic neurons lack tonic currents. Furthermore, in these neurons, δ subunit-selective activators (i.e., THIP and allopregnanolone) produced less current in RQ compared to RR, suggesting dysfunction of δ subunit-containing receptors. Although Western blotting did not reveal a reduction in δ subunit surface trafficking, it did show a reduction in total δ subunit expression along with a reduction of α4 subunit trafficking, which is the partner for the δ subunit required to form functional receptors that mediate tonic inhibition in thalamic neurons. Without being held to theory, it is believed that the loss of tonic inhibition in cortical and thalamic neurons in mice expressing the mutant γ2R43Q subunit is caused by a dysregulation of the assembly/trafficking of non-mutant subunits, namely α5 in cortex and α4 and δ in thalamus.

Reduction of inhibitory tonic currents is linked to membrane depolarization, increased neuronal firing and enhanced synaptic summation. The findings that RQ somatosensory cortical layer II/III neurons lack inhibitory tonic current and exhibit increased firing rates are consistent with these previous conclusions and with the hyperexcitable cortex of human subjects harboring the γ2R43Q mutation. Although cortex and thalamus are both involved in SWDs, cortical hyperexcitability appears to be a prerequisite for SWD generation, and thus the loss of cortical tonic inhibition may be a key cause of the increased intracortical excitability, increased facilitation, and the development of SWDs seen in humans harboring the γ2R43Q mutation.

Thalamic relay neurons can function in either tonic or burst firing modes depending on the average membrane potential, which in turn can be influenced by the level of GABAergic tonic current. Thus, depolarization resulting from the loss of tonic inhibition may shift thalamic neurons away from burst firing mode. Consistent with this idea, the multielectrode recordings revealed that RQ thalamic neurons have a reduced probability of burst firing compared with RR. Interestingly, the average thalamic firing rate was lower in RQ than in RR, suggesting that the depolarization caused by loss of tonic inhibition is relatively subtle: enough to reduce burst firing but not enough to itself promote strong tonic firing. Furthermore, selective blockade of cortical tonic inhibition with L655,708 increases the firing rate in cortex only, leaving thalamic firing and the bursting behaviors in both cortex and thalamus unaffected. Taken together, these results suggest that cortical and thalamic tonic inhibition have distinct and separable roles in regulating thalamocortical circuit function.

Previous work demonstrates a correlation between absence seizures and enhanced tonic inhibition in thalamic relay neurons of several rodent models, leading to the conclusion that enhanced tonic GABAergic inhibition is a "necessary and sufficient condition for nonconvulsive typical absence seizure generation". However, the finding that γ2R43Q knock-in mice entirely lack tonic inhibition in thalamic relay neurons demonstrates that enhanced thalamic tonic inhibition is not necessary to produce absence seizures. Instead, together with the aforementioned work, the present data suggest that an optimal level of tonic inhibition throughout the thalamocortical circuit is necessary for normal thalamocortical processing, such that either increases or decreases away from this optimum are sufficient to enhance susceptibility to absence epilepsy. Importantly, it has also been shown that cortical tonic inhibition is absent and that cortical neurons have elevated firing rates in RQ mice. Future genetic or pharmacological models of region-specific deficits in tonic inhibition will be helpful for dissecting the contributions of tonic inhibition in cortex versus thalamus to regulating absence epilepsy.

Despite the absence of endogenous tonic inhibition, it has been shown that the δ subunit-selective activators THIP and allopregnanolone can recruit tonic currents in both thalamus and cortex of RQ mice. Without being held to theory, it is proposed that absence epilepsies can be divided into multiple classes, two distinct examples of which are characterized by either an increase or a decrease (e.g., γ2R43Q) in tonic inhibition. Therefore, appropriately titrated doses of tonic current activators may have high therapeutic benefit for rescuing normal function in the latter class.

Example 6

RQ Mice Express the SWDs Associated with Absence Epilepsy

Figure 6:
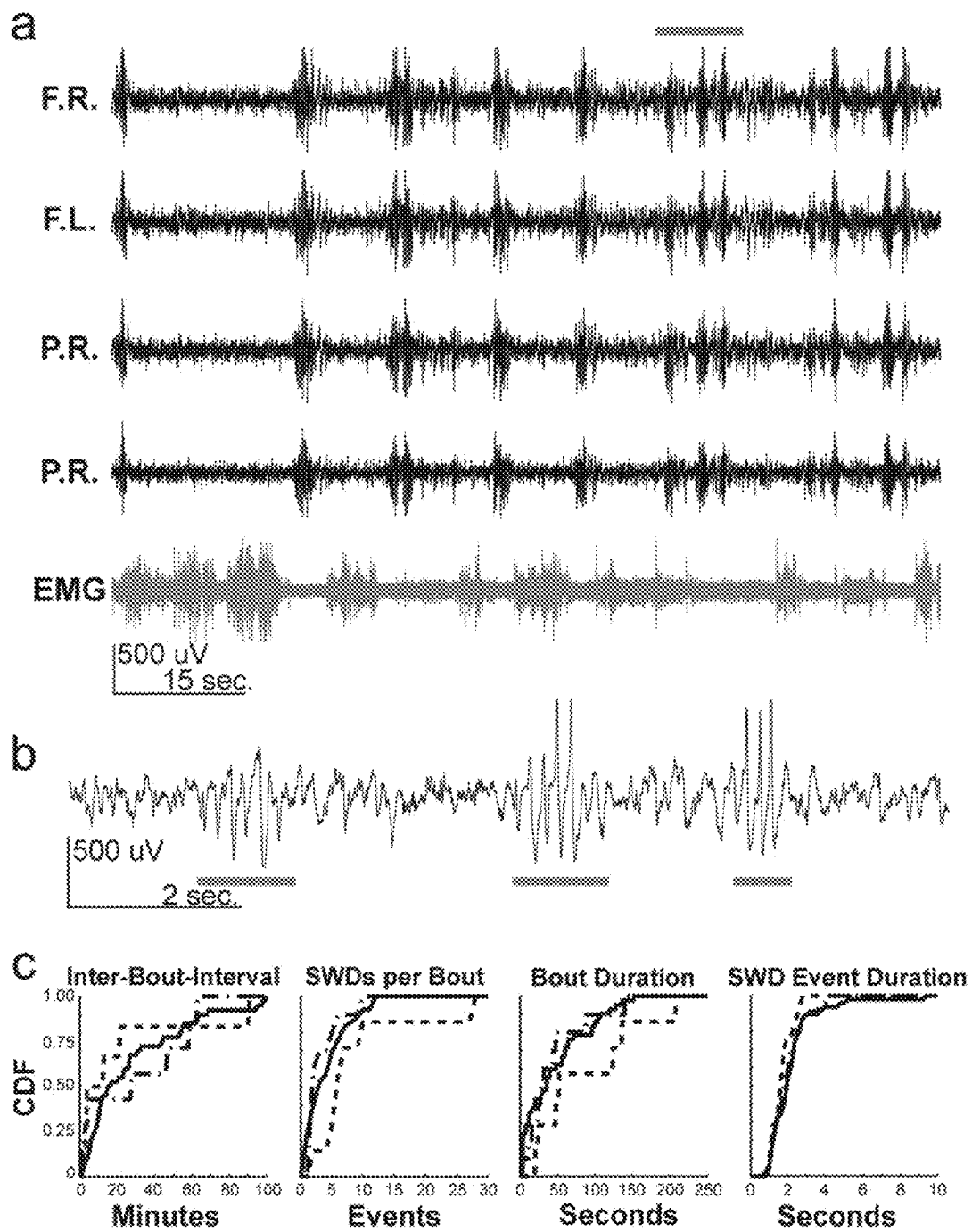
FIG. 6 shows that RQ mice express SWDs (spike-and-wave EEG discharges) associated with Absence epilepsy. Panel a) Electroencephalogram (EEG) recording of an RQ mouse. Top trace to bottom trace: frontal right cortex (F.R.); frontal left cortex (F.L.); parietal right cortex (P.R.); parietal left cortex (P.L.); electromyogram (EMG). Note the brief yet high number (approximately 11 times during the 1.5 minute trace) of synchronized events that occur across all EEG leads during the absence of signal in the EMG. Panel b) Expanded F.R. EEG recording from grey bar in A (10 seconds). Note the brief approximately 6 Hz SWD events (grey bars) that occur 3 times during the 10-second trace. Panel c) Cumulative distributions from three different RQ mice (solid, dashed, and dash-dotted lines represent each mouse) show similar characteristics from all animals for inter-bout-interval, SWDs per bout, bout duration and SWD event duration. SWDs were not observed in litter-mate control mice (not shown).

The γ2R43Q mutation confers absence seizures and generalized EEG SWDs in humans and knock-in (RQ) mice. Presented herein is evidence of these bilateral, synchronous (approximately 6 Hz) SWDs in RQ mice using continuous EEG and EMG recordings (FIG. 6). Quantification was done off-line after recordings were completed. SWDs were assessed for individual event duration (seconds), inter-bout-intervals (IBI: minutes), events per bout, and bout duration (seconds). A 'bout' was classified as two or more individual SWD events occurring <30 seconds apart. FIG. 6 shows EEG and EMG recordings from one RQ mouse during a SWD bout (FIG. 6, panels a and b), along with quantified SWD assessment for three different (solid, dashed & dashed-dotted lines) RQ mice (FIG. 1, panel c) (mouse: median [25%: 75%] n) (IBI in minutes: A: 16.2 [8.4:44.5] 40; B: 8.7 [3.7:21.5] 6; C: 27.5, 2.9:59.1, 7) (Events per bout: A: 3 [1:6.5] 42; B: 6 [3.5:10, 7] C: 2 [0:5.5] 10) (Bout duration in seconds: A: 36 [6:72] 42; B: 52 [24:136] 7; C: 30 [16:43] 10) (Event duration in seconds: A: 2 [1.4:2.5] 50; B: 1.7 [1.3:1.9] 14; C: 1.9 [1.4:2.5] 24). All RQ mice assessed with EEG and EMG monitoring presented synchronized SWDs across all EEG leads with the coinciding lack of EMG activity. No SWDs were seen in naïve wild-type (RR) mice EEG recordings.

Example 7

Blocking Cortical Tonic Inhibition Produces SWDs in Wild-Type Mice

Figure 7:
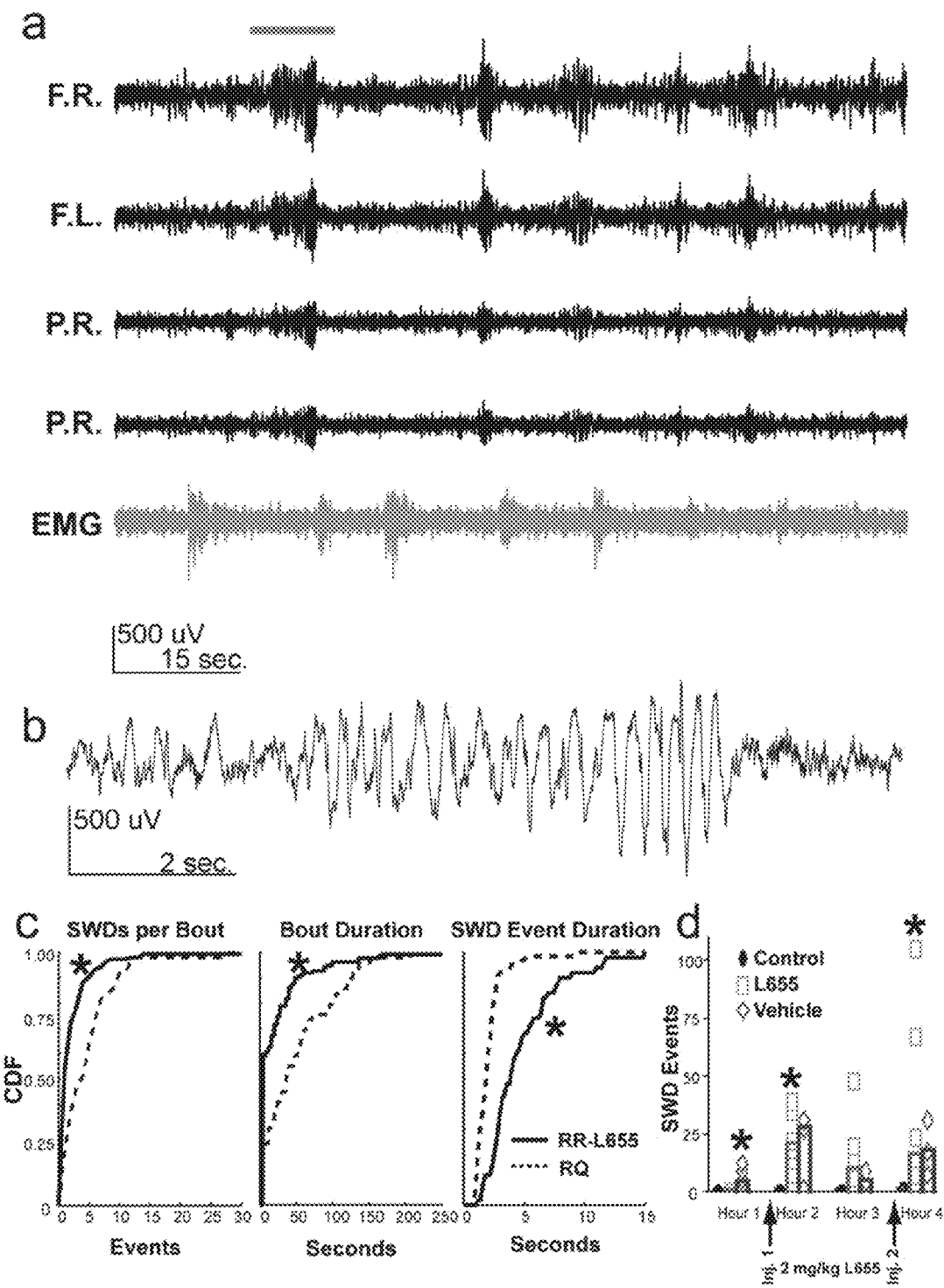
FIG. 7 shows that blocking cortical tonic inhibition produces SWDs in wild-type mice. Panel a) Electroencephalogram (EEG) recording of a wild-type (RR) mouse i.p. injected with 2 mg/kg of the $GABA_{(A)}$ receptor α5-subunit-selective inverse-agonist L655,708 (RR-L655). Similar to RQ mice, note the brief yet high number (approximately 6 times during the 1.5 minute trace) of synchronized events that occur across all EEG leads during the absence of signal in the EMG. Panel b) Expanded F.R. EEG recording from grey bar in A (10 seconds) displays a brief approximately 6 Hz SWD event (grey bar). Panel c) Cumulative distributions shows RR-L655 mice display significantly less SWDs per bout ($p<0.05$), shorter bout durations ($p<0.05$), yet longer SWD event durations ($p<0.05$) than RQ mice (dotted line). Panel d) Quantification of SWD events shows RR-L655 mice did not display SWDs prior to L655,708 injection (Hour 1), but did show SWDs after each hour of injection (Hour 2, $p<0.05$; Hour 4, $p<0.05$). Interestingly, SWDs were still present in RR-L655 mice 3 days after the last L655,708 treatment (vehicle: Hour 1, $p<0.05$).

Previous research has demonstrated a positive correlation between SWDs and thalamic inhibitory tonic currents, a finding which led to the conclusion that enhanced GABAergic tonic inhibition is a "necessary" condition for typical absence-associated SWD generation. The data presented herein shows that not only is altering thalamic inhibitory tonic currents not a "necessary" condition to produce SWDs, but that the selective pharmacological block of cortical tonic inhibition is enough to produce SWDs in RR mice (FIG. 7). Intraperitoneal (i.p.) administration of the α5-subunit-selective inverse-agonist L655,708 (L655) at a concentration (2 mg/kg) previously shown to bind the majority of receptors responsible for generating inhibitory tonic currents in somatosensory cortical layer II/III principal neurons produced SWDs (approximately 6 Hz) in RR mice (RRL6) that are electrographically similar to SWDs seen in RQ mice (FIG. 7, panels a and b). However, although similar in frequency, L655 induced SWDs (L6-SWDs) display fewer events per bout (RQ: 3 [2:6] 59; L6:1 [0:3] 155; p<0.001) and shortened bout durations (RQ: 36 [12:80] 59; RRL6:4 [0:36] 137; p<0.001) compared to RQ, while individual L6-SWD event duration was longer (RQ: 1.9 [1.4:2.4] 64; RRL6:4.0 [2.8: 6.5] 50; p<0.001).

Example 8

GABA$_A$ Receptor δ-Subunit Selective Agonists Rescue Tonic Inhibition in RQ Cortical Principal Neurons Although RQ principal neurons lack inhibitory tonic currents, previous research also discovered that multiple GABA$_A$ receptor agonists, at concentrations selective to δ-subunit-associated GABA$_A$ receptors (1 µM THIP, 30 nM allopregnanolone (ALLO); FIG. 8, panel a), were able to produce a holding current in RQ cortical neurons. This finding argues for the presence of a functional level of δ-subunit-associated GABA$_A$ receptors in RQ cortical neurons. Using whole-cell patch-clamp recordings, a low concentration (10 nM) of Ganaxolone (GANX) (FIG. 8, panel b), the synthetic neuroactive steroid related to ALLO, produces an inhibitory holding current (FIG. 8, panel c) (left axis: mean±SEM in pA, n; RR: 6.1±0.58, 5; RQ: −0.8±1.0, 5, p<0.05; 100 nM THIP-RQ: 6.5±1.7, 4; 1 µM THIP-RQ: 23.88±2.2, 5, p<0.05; 10 nM GANX-RQ: 9.8±2.5, 4) and current density (right axis: mean±SEM in pA/pF, n; RR: 0.56±0.11, 5; RQ: −0.11±0.16, 5, p<0.05; 100 nM THIP-RQ: 0.36±0.16, 4; 1 µM THIP-RQ: 1.3±0.14, 5, p<0.05; 10 nM GANX-RQ: 0.38±0.08, 4) in RQ cortical neurons equal to the inhibitory tonic current seen in RR cortical neurons. Thus, although RQ cortical layer II/III principal neurons lack GABAergic tonic inhibition, these neurons still possess an ability to produce normal levels of inhibitory tonic current via δ-subunit-associated GABA$_A$ receptor activation.

Example 9

Rescuing Cortical Tonic Inhibition Attenuates SWDs in RQ Mice

Over-activating the δ-subunit-associated GABAergic tonic current (THIP) in the thalamus of wild-type mice produces the SWDs associated with absence epilepsy. On the other hand, research has also uncovered that administration of δ-subunit-selective agonists (ALLO and GANX) directly into somatosensory cortex of SWD-expressing WAG/Rij mice decreases the number of SWDs observed in these mice. Activating the available δ-subunit-associated inhibitory tonic current in RQ mice (FIG. 8) with a very low concentration (2 mg/kg) of GANX attenuates SWDs in RQ mice (FIG. 9).

EEG monitored RQ mice were i.p. injected twice a day with GANX or THIP 4 times over a 7 day period (FIG. 9, panel a). Multiple concentrations of GANX (2 and 5 mg/kg) and THIP (0.5 and 1.5 mg/kg) were tested for their ability to suppress SWD expression and only the lowest concentration (2 mg/kg) of GANX was statistically effective in decreasing RQ-SWD expression (FIG. 9, panel b) (SWD events per hour: median[25%: 75%] n; RQ: 9.0 [7.0:19.0] 16; 2 mg/kg GANX-RQ: 3.0 [0.5:6.5] 6, p<0.05; 5 mg/kg GANX-RQ: 5.0 [3.0:6.0] 4; 0.5 mg/kg THIP-RQ: 9.5 [3.5:19.0] 4; 1.5 mg/kg THIP-RQ: 7.5 [4.0:17.5] 4). The 2 mg/kg GANX treatment also decreased bout duration (seconds; RQ: 36 [12:80] 59; 2 mg/kg GANX-RQ: 12 [4:46, 30] p<0.05) and event duration (seconds; RQ: 1.9 [1.4:2.4] 88; 2 mg/kg GANX-RQ: 1.4 [1.0:2.0] 64, p<0.001), but did not effect the number of SWDs per bout (events; RQ: 3 [2:6] 59; 2 mg/kg GANX-RQ: 2 [1:5] 27).

Discussion of Examples 6-9

The major finding from this study is that the loss (RQ) (FIG. 6) or decrease (RR-L655) (FIG. 7) of cortical tonic inhibition results in a SWD-expressing phenotype, while normal expression (RR: FIG. 8, panel c) presents a SWD-free phenotype and pharmacological replacement of cortical tonic inhibition (RQ-GANX: FIG. 8, panel c) suppresses SWD expression (FIG. 9). These findings are consistent with the conclusion that the amount of cortical tonic inhibition regulates SWD expression. Furthermore, the discovery of a treatment (low-levels GANX), coupled with the previous discoveries of the mechanisms underlying how the γ2R43Q mutation results in a pro-epileptic neuronal environments, presents an avenue of 'personalized medicine' for this condition, spanning from genome to treatment.

The findings presented herein suggest that SWD expression is not linked to any one tonic current-associated GABA$_A$ receptor-subtype (α5 or δ) in the cortex, but rather is linked, in general, to cortical tonic inhibitory tone. Rescuing RQ cortical tonic inhibition, and the subsequent decrease in SWD expression, via activation of δ-subunit-associated GABA$_A$ receptors with GANX, supplies the evidence that SWD expression is not solely under control of cortical α5-subunit-associated inhibition. Conversely, the selective decrease/block of α5-subunit-associated inhibition (RR-L655), which also results in SWD expression (FIG. 7), supplies the evidence that SWD expression is not solely under control of cortical δ-subunit-associated inhibition, either. These results are consistent, however, with the conclusion that SWD expression is regulated by general cortical tonic inhibitory tone.

Recent research suggests that SWD expression is not the only pathology linked to cortical tonic inhibitory tone. Therapeutic treatments that disrupt cortical tonic inhibition (L655, α5IA, GABA$_B$ receptor antagonists) display cognitive enhancing ability and are being investigated as treatments for cognitive disorders such as Downs Syndrome, though SWDs and absence seizures should now be considered as potential side-effects for this treatment. Additionally, pharmacological agents that activate cortical tonic inhibition through various avenues (THIP, GANX, GABA$_B$ receptor agonists) are currently being investigated as treatments for Fragile X, Rett syndrome, schizophrenia and autism. In these cases, similar to SWD regulation, it may simply be the increase of the cortical tonic inhibitory tone, manifested via any mechanism, which is needed to temper these disorders. A more comprehensive analysis of GABAergic tonic transmission in these pathologies will help tailor appropriate treatments.

Absence seizures have recently been linked to increases in δ-subunit-associated GABA$_A$ receptor activation in thalamic relay neurons. Born from this evidence is the theory that the resulting persistent hyperpolarization of thalamic relay neurons makes relay neurons more susceptible to rhythmic bursting and insensitive to sensory input and, thus, is necessary to tip the system balance towards a gain-of-function in the cortico-thalamic network. However, in vitro examination of T-type calcium bursting (T-bursts) behaviors in thalamocortical mouse brain slices detected a decrease or no change in thalamic T-bursting behaviors compared to control for RQ and L655-treated (RR) brain slices, respectively. These results suggest that neither increased thalamic inhibitory tone nor the resulting increased susceptibility to rhythmic bursting is essential for SWD expression. Furthermore, levels of tonic inhibition in principal cortical cells have yet to be investigated in absence epilepsy animal models (GAERS, stargazer, lethargic, tottering) that do express increased thalamic tonic inhibitory currents. Although increases above normal levels of tonic inhibitory currents in thalamus may be enough to provoke SWDs and absence seizures, evidence suggests that activation or rescue of missing tonic inhibitory tone in the principal cortical neurons of these animals may be enough to ward off SWD expression.

Lastly, but definitely not least, the data included herein provides evidence of long-lasting aberrant thalamocortical function after inducing SWDs with L655 in wild-type mice. Mice that were injected twice a day for 2 consecutive days with L655 still displayed SWDs 3 days after the last injection (FIG. 7, panel d: vehicle, Hour 1, p<0.05). This lingering malfunction of the post-epileptic thalamocortical circuit suggests that pro-epileptic homeostatic changes occur, changes observed in other epilepsy-induced animal models that can include a down-regulation of α5-subunit-associated GABA$_A$ receptor expression. This result gives extra credence to providing the earliest possible, but appropriately tailored, therapeutic intervention for individuals suffering from CAE.

Example 10

Evaluation of Sleep Patterns in RQ Mice Injected with GANX

RQ mice had significantly (p<0.05, Kruskal-Wallis test with Tukey post-hoc tests) briefer Wake durations than RR, which was not reversed by GANX. RQ mice also had shorter durations of single NREM episodes than RR, and this was reversed by GANX to normal levels. No groups differed in durations of REM. RQ mice experienced shorter "brief awakenings" (<=16 seconds) than RR, and this was not altered by GANX, whereas the number of brief awakenings did not differ between any groups. During normal sleep time (daylight), RQ had higher normalized delta power than RR, and this was reversed by GANX toward normal levels. Higher delta power and shorter brief awakenings during NREM sleep could be indicative of higher "sleep pressure" (i.e., a homeostatic drive to compensate for insufficient sleep).

Figure 10:
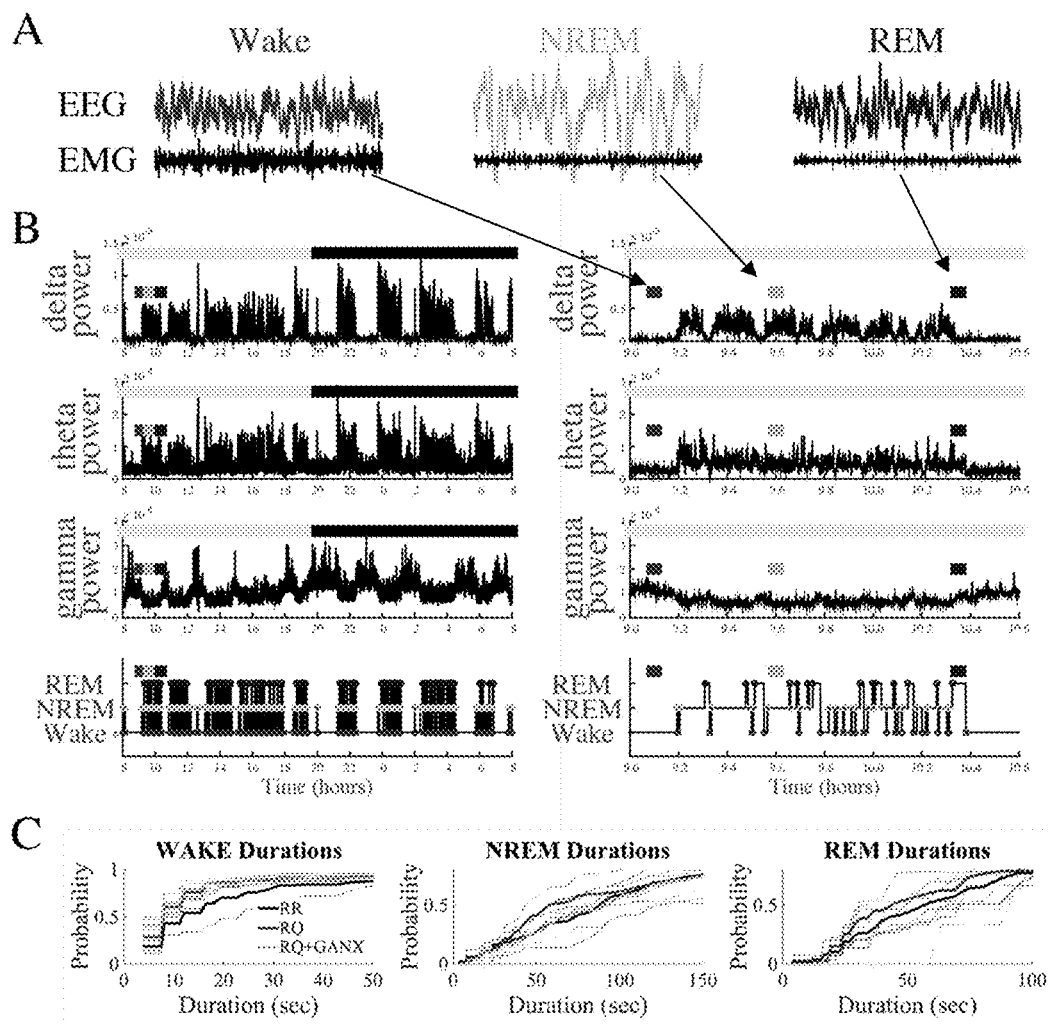
FIG. 10 shows that RQ mice have altered sleep compared to wild type littermates, and that some of these alterations can be reversed by low-dose ganaxolone. Panels A & B show an example determination of sleep stages from EEG and EMG data in a wild type mouse, including analysis of EEG power in different frequency bands, and the hypnogram of sleep stages, during a typical 24 hour recording period. Panel C shows the distributions of Wake, NREM and REM durations during normal sleep time for wild type RR mice, mutant RQ mice and mutant RQ mice after injection with low-dose ganaxolone (2.5 mg/kg i.p.). Ganaxolone significantly reversed alterations in NREM durations and alterations in delta power back toward normal levels.

FIG. 10 shows that RQ mice display alterations in NREM sleep that can be reversed by low-dose ganaxolone. A) Example EEG and EMG epochs (4 sec) from a WT mouse, taken during the time points marked in B by the arrows. B) (left panels) Power in the delta (0.5-4 Hz), theta (6-9 Hz) and gamma (20-100 Hz) bands, and the hypnogram of sleep stages as determined from the EEG and EMG by an experienced scorer, during a 24 hour recording period. Normal sleep time (daylight) is indicated by the grey bar, and night is indicated by the black bar. (right panels) Expansion of the first sleep period, marked by colored bars in A. C) Distributions of Wake, NREM and REM periods for 3 WT and 3 RQ mice and for the same RQ mice after ganaxolone treatment (2 mg/kg i.p.). Dashed lines represent individual mice, and solid lines represent the mean for each condition. During normal sleep time, RQ mice had significantly (p<0.05, Kruskal-Wallis test with Tukey post-hoc test) briefer Wake and NREM durations than WT mice, and the NREM durations were returned to normal by ganaxolone.

These data indicate that sleep alterations accompany absence epilepsy in RQ mice, particularly affecting NREM sleep. The alterations in NREM sleep are reversed by GANX. Selective pharmacological manipulation of tonic inhibition using GANX is thus expected to be a useful avenue for treating both seizures and sleep disorders.

DEFINITIONS

GABA$_A$ receptor-a ligand-gated ion channel. The endogenous ligand is γ-aminobuyric acid (GABA).

RQ- and RR-strains of C57BL/6J mice. RQ are the γ2R43Q knock-in mice that serve as a model for absence epilepsy.

ALLO—allopregnalone. An endogenous neurosteroid with preferentially high efficacy for enhancing activation of δ subunit-dependent tonic inhibition.

GANX—ganaxolone. A synthetic analogue of ALLO.

THIP—4,5,6,7-tetrahydroisoxazolo[5,4-c]pyridin-3-ol. An agonist with selectively high efficacy for activating δ subunit-dependent tonic inhibition.

L655,708-11,12,13,13a-Tetrahydro-7-methoxy-9-oxo-9H-imidazo[1,5-a]pyrrolo[2,1-c][1,4]benzodiazepine-1-carboxylic acid, ethyl ester. An inverse agonist of the benzodiazepine site that selectively blocks α5 subunit-dependent tonic inhibition.

IPSC—inhibitory postsynaptic currents—synaptic currents that make a postsynaptic neuron less likely to generate an action potential.

Interevent interval (IEI)—The probability that two successive events (e.g., mIPSCs or SWDs) will occur separated by a specified time interval. Typically expressed as a histogram showing the distribution, or cumulative distribution, of probabilities over a range of intervals.

SWD—spike- and wave EEG discharge i.p. —intraperitoneal

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of treating absence epilepsy in a mammalian subject in need thereof, comprising administering ganaxolone to the mammalian subject in an amount of 0.2 to 2 mg/kg per dose, wherein the mammalian subject has been diagnosed with absence epilepsy, wherein the epilepsy is characterized by a deficit in tonic inhibition.

2. The method of claim 1, wherein the mammalian subject has a γ2R43Q mutation in the $GABA_A$ receptor.

3. The method of claim 1, wherein the mammalian subject is a human pediatric subject.

4. The method of claim 3, wherein the human pediatric subject with absence epilepsy is 1 to 18 years of age, and has an average weight of 10 to 80 kg and the dose of ganaxolone is 2 to 160 mg per administration.

5. The method of claim 1, wherein the mammalian subject suffers from nonconvulsive seizures associated with loss of consciousness, glassy-eyed staring, spike and wave EEG discharges, or a combination thereof.

6. The method of claim 1, wherein the mammalian subject is resistant to standard antiabsence drug therapy.

* * * * *